US012018254B2

United States Patent
Raman et al.

(10) Patent No.: US 12,018,254 B2
(45) Date of Patent: Jun. 25, 2024

(54) METHODS OF MAKING UNBIASED PHAGE LIBRARIES

(71) Applicant: Wisconsin Alumni Research Foundation, Madison, WI (US)

(72) Inventors: Srivatsan Raman, Middleton, WI (US); Phil Huss, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 312 days.

(21) Appl. No.: 17/386,176

(22) Filed: Jul. 27, 2021

(65) Prior Publication Data

US 2022/0025360 A1    Jan. 27, 2022

Related U.S. Application Data

(60) Provisional application No. 63/057,006, filed on Jul. 27, 2020.

(51) Int. Cl.
*C40B 50/06* (2006.01)
*C12N 9/22* (2006.01)
(Continued)

(52) U.S. Cl.
CPC .......... *C12N 15/1093* (2013.01); *C12N 9/22* (2013.01); *C12N 15/102* (2013.01); *C12N 15/11* (2013.01);
(Continued)

(58) Field of Classification Search
CPC .......... C12N 15/1093; C12N 15/1034; C12N 15/1037; C12N 15/102; C12N 15/11;
(Continued)

(56) References Cited

U.S. PATENT DOCUMENTS

2009/0253896 A1    10/2009   Smith et al.

FOREIGN PATENT DOCUMENTS

| WO | WO-02092780 A2 * | 11/2002 | ........... C12N 15/102 |
| WO | WO-2006058159 A2 * | 6/2006 | ......... C12N 15/1037 |
| WO | WO-2018232017 A1 * | 12/2018 | ............. A61K 48/00 |

OTHER PUBLICATIONS

Abedon, S.T.; "Lysis from without"; Bacteriophage, vol. 1; 2011; pp. 46-49.

(Continued)

*Primary Examiner* — Christian C Boesen
(74) *Attorney, Agent, or Firm* — Karen A. LeCuyer; DeWitt LLP

(57) ABSTRACT

Described herein is a method of preparing an unbiased library of phage variants, comprising (a) preparing a population of "acceptor phage"; (b) removing an endogenous target gene and inserting gene variants into the acceptor phage genomes; (c) enriching the recombined phages; and (d) expressing the library for selection. The acceptor phage is a lytic phage comprising a synthetic genome wherein the target gene of interest is flanked by recombinase sites. The acceptor phage infects a first host bacteria expressing a recombination plasmid facilitating recombination. The phages then infect a second host bacteria expressing a counterselection system that accumulates recombined phage variants and selecting against non-recombined phages. The accumulated phage variants infect a third host bacteria. The phage library may then be sequenced and characterized.

13 Claims, 26 Drawing Sheets

Specification includes a Sequence Listing.

(51) Int. Cl.
    *C12N 15/10* (2006.01)
    *C12N 15/11* (2006.01)
(52) U.S. Cl.
    CPC .................... *C12N 2310/20* (2017.05); *C12N 2795/10052* (2013.01)
(58) Field of Classification Search
    CPC ...... C12N 15/10; C12N 9/22; C12N 2310/20; C12N 2795/10052
    See application file for complete search history.

(56) References Cited

OTHER PUBLICATIONS

Ando, H., et al.; "Engineering Modular Viral Scaffolds for Targeted Bacterial Population Editing"; Cell Systems. vol. 1; 2015; pp. 187-196.
Arthur, M., et al.; "Restriction fragment length polymorphisms among uropathogenic *Escherichia coli* isolates: pap-related sequences compared with rrn operons"; Infection and Immunity, vol. 58, Issue No. 2; 1990; pp. 471-479.
Baba, T., et al.; "Construction of *Escherichia coli* K-12 in-frame, single-gene knockout mutants: the Keio collection"; Molecular Systems Biology, vol. 2, Article No. 2006.0008; 2006; 11 pages.
Clokie, M., et al.; "Phages in nature"; Bacteriophage, vol. 1; 2011; pp. 31-45.
Davidson, T. et al.; "Phage Display to Augment Biomaterial Function"; International Journal of Molecular Sciences, vol. 21; 2020; 17 pages; doi: 10.3990/ijms21175994.
De Jonge, P., et al.; "Molecular and Evolutionary Determinants of Bacteriophage Host Range"; Trends in Microbiology, vol. 27, Issue No. 1; 2019; pp. 51-63.
Dedrick, R., et al.; "Engineered bacteriophages for treatment of a patient with a disseminated drug-resistant Mycobacterium abscessus"; Nature Medicine, vol. 25, Issue No. 5; 2019; pp. 730-733.
Dedrick, R., et al.; "Mycobacteriophage ZoeJ: A broad host-range close relative of mycobacteriophage TM4"; Tuberculosis, vol. 115; 2019; pp. 14-23.
Dunne, M., et al.; "Reprogramming Bacteriophage Host Range through Structure-Guided Design of Chimeric Receptor Binding Proteins"; Cell Reports, vol. 29; 2019; pp. 1336-1350.
Durfee, T., et al.; "The Complete Genome Sequence of *Escherichia coli* DH10B: Insights into the Biology of a Laboratory Workhorse"; Journal of Bacteriology, vol. 190, Issue No. 7; 2008; pp. 2597-2606.
Edgar, R., et al.; "Error filtering, pair assembly and error correction for next-generation sequencing reads"; Bioinformatics, vol. 31, Issue No. 21; 2015; pp. 3476-3482.
Fowler, D., et al.; "Deep mutational scanning: a new style of protein science"; Nature Methods, vol. 11, Issue No. 8; 2014; pp. 801-807.
Fraser, J., et al.; "Ig-like domains on bacteriophages: a tale of promiscuity and deceit"; Journal of Molecular Biology, vol. 359; 2006; pp. 496-507.
Fraser, J., et al.; "Immunoglobulin-like domains on bacteriophage: weapons of modest damage?"; Current Opinion in Microbiology, vol. 10; 2007; pp. 382-387.
Garcia, E., et al.; "The genome sequence of Yersinia pestis bacteriophage phiA1122 reveals an intimate history with the coliphage T3 and T7 genomes"; Journal of Bacteriology, vol. 185, Issue No. 17; 2003; pp. 5248-5262.
Garcia-Doval, C., et al.; "Structure of the receptor-binding carboxy-terminal domain of bacteriophage T7 tail fibers"; PNAS, vol. 109, Issue No. 24; 2012; pp. 9390-9395.
Gietz, R. et al.; "Transformation of yeast by lithium acetate/single-stranded carrier DNA/polyethylene glycol method"; Methods in Enzymology, vol. 350; 2002; pp. 87-96.
González-García, V., et al.; "Characterization of the initial steps in the T7 DNA ejection process"; Bacteriophage, vol. 5, Issue No. 3; 2015; 7 pages.

Heineman, R. et al.; "Optimal foraging by bacteriophages through host avoidance"; The American Naturalist, 171, Issue No. 4; 2008; pp. E149-157.
Holtzman, T., et al.; "A continuous evolution system for contracting the host range of bacteriophage T7"; Scientific Reports, vol. 10, Issue No. 307; 2020; 8 pages; doi: https://doi.org/10.1038/s41598-019-57221-0.
Huss, P. et al.; "Mapping the functional landscape of the receptor binding domain of T7 bacteriophage by deep mutational scanning"; eLife, vol. 10, e63775; 2021; 30 pages; doi: https://doi.org/10.7554/eLife.63775.
International Search Report and Written Opinion for International Application PCT/US2021/043282; International Filing Date: Jul. 27, 2021; Date of Mailing: Nov. 29, 2021; 13 pages.
Jaschke, P., et al.; "A fully decompressed synthetic bacteriophage øX174 genome assembled and archived in yeast"; Virology, vol. 434; 2012; pp. 278-284.
Jiang, W., et al.; "RNA-guided editing of bacterial genomes using CRISPR-Cas systems"; Nature Biotechnology, vol. 31, Issue No. 3; 2013; pp. 233-239.
Kang, H.-W., et al.; "Wksl3, a New Biocontrol Agent for *Salmonella enterica* Serovars Enteritidis and Typhimurium in Foods: Characterization, Application, Sequence Analysis, and Oral Acute Toxicity Study"; Applied Environmental Microbiology, vol. 79, Issue No. 6; 2013; pp. 1956-1968.
Khan Mirzaei, M., et al.; "Isolation of Phages for Phage Therapy: A Comparison of Spot Tests and Efficiency of Plating Analyses for Determination of Host Range and Efficacy"; PLoS ONE, vol. 10, Issue No. 3; 2015; 13 pages.
Kilcher, S., et al.; "Cross-genus rebooting of custom-made, synthetic bacteriophage genomes in L-form bacteria"; PNAS, vol. 115, Issue No. 3; 2018; pp. 567-572.
Kilcher, S., et al.; "Engineering Bacteriophages as Versatile Biologics"; Trends in Microbiology, vol. 27, Issue No. 4; 2019; pp. 355-367.
Kosuri, S., et al.; "Composability of regulatory sequences controlling transcription and translation in *Escherichia coli*"; PNAS, vol. 110, Issue No. 34; 2013; pp. 14024-14029.
Kuijpers, N., et al.; "A versatile, efficient strategy for assembly of multi-fragment expression vectors in *Saccharomyces cerevisiae* using 60 bp synthetic recombination sequences"; Microbial Cell Factories, vol. 12, Issue No. 47; 2013; 13 pages.
Langer, S., et al.; "A genetic screen identifies novel non-compatible IoxP sites"; Nucleic Acids Research, vol. 30, Issue No. 14; 2002; pp. 3067-3077.
Lee, J., et al.; "Deep mutational scanning of hemagglutinin helps predict evolutionary fates of human H3N2 influenza variants"; PNAS, vol. 115, Issue No. 35; 2018; pp. E8276-E8285.
Lin, T.-Y., et al.; "A T3 and T7 Recombinant Phage Acquires Efficient Adsorption and a Broader Host Range"; PLOS ONE, vol. 7, Issue No. 2, e30954; 2012; 10 pages.
Magoč, T., et al.; "FLASH: fast length adjustment of short reads to improve genome assemblies"; Bioinformatics, vol. 27, Issue No. 21; 2011; pp. 2957-2963.
Marinelli, L., et al.; "BRED: A Simple and Powerful Tool for Constructing Mutant and Recombinant Bacteriophage Genomes"; PLOS ONE, vol. 3, Issue No. 12, e3957; 2008; 8 pages.
Meyer, J., et al.; "Repeatability and Contingency in the Evolution of a Key Innovation in Phage Lambda"; Science, vol. 335; 2012; pp. 428-432.
Molineux, I.; "No. syringes please, ejection of phage T7 DNA from the virion is enzyme driven"; Molecular Microbiology, vol. 40, Issue No. 1; 2001; pp. 1-8.
Nobrega, F., et al.; "Targeting mechanisms of tailed bacteriophages"; Nature Reviews Microbiology, vol. 16; 2018; pp. 760-773.
Pagnout, C., et al.; "Pleiotropic effects of rfa-gene mutations on *Escherichia coli* envelope properties"; Scientific Reports, vol. 9, Issue No. 9696; 2019; 16 pages.
Pires, D., et al.; "Genetically Engineered Phages: a Review of Advances over the Last Decade"; Microbiology and Molecular Biology Reviews, vol. 80, Issue No. 3; 2016; pp. 523-543.

(56) References Cited

OTHER PUBLICATIONS

Principi, N., et al.; "Advantages and Limitations of Bacteriophages for the Treatment of Bacterial Infections"; Frontiers in Pharmacology, vol. 10, Article No. 513; 2019; 9 pages.

Qimron, U., et al.; "Genomewide screens for *Escherichia coli* genes affecting growth of T7 bacteriophage"; PNAS, vol. 103, Issue No. 50; 2006; pp. 19039-19044.

Sausset, R., et al.; "New insights into intestinal phages"; Mucosal Immunology, vol. 13; 2020; pp. 205-215.

Schooley, R., et al.; "Development and Use of Personalized Bacteriophage-Based Therapeutic Cocktails to Treat a Patient with a Disseminated Resistant Acinetobacter baumannii Infection"; Antimicrobial Agents and Chemotherapy, vol. 61, Issue No. 10, e00954-17; 2017; 14 pages.

Shen, T.-C., et al.; "Engineering the gut microbiota to treat hyperammonemia"; The Journal of Clinical Investigation, vol. 125, Issue No. 7; 2015; pp. 2841-2850.

Sugimura, Y., et al.; "Screening for the Preferred Substrate Sequence of Transglutaminase Using a Phage-displayed Peptide Library"; Journal of Biological Chemistry, vol. 281, Issue No. 26; 2006; pp. 17699-17706.

Valvano, M., et al.; "Novel pathways for biosynthesis of nucleotide-activated glycero-manno-heptose precursors of bacterial glycoproteins and cell surface polysaccharides"; Microbiology, vol. 148, ; 2002; pp. 1979-1989.

Yehl, K., et al.; "Engineering Phage Host-Range and Suppressing Bacterial Resistance through Phage Tail Fiber Mutagenesis"; Cell, vol. 179; 2019; pp. 459-469.e1-e9.

Yosef, I., et al.; "Extending the Host Range of Bacteriophage Particles for DNA Transduction"; Molecular Cell, vol. 66; 2017; pp. 721-728.e1-e3.

Coyote-Maestas and Fraser. ORACLE reveals a bright future to fight bacteria. eLife, 2021; 10:e68277. DOI: https://doi.org/10.7554/eLife.68277.

Hille, Frank, et al. The Biology of CRISPR-Cas: Backward and Forward, Cell, 2017, 172, pp. 1239-1259.

Oliveira, Pedro H., et al. The interplay of restriction-modification systems with mobile genetic elements and their prokaryotic hosts, Nucleic Acids Research, 2014, vol. 42, No. 16, pp. 10618-10631.

Stokar-Avihail, Avigail, et al. Discovery of phage determinants that confer sensitivity to bacterial immune systems, 2023, Cell 186, 1863-1876.

\* cited by examiner

METHODS OF MAKING UNBIASED PHAGE LIBRARIES

CROSS-REFERENCE TO RELATED APPLICATIONS

This application claims priority to U.S. Provisional Application 63/057,006 filed on Jul. 27, 2020, which is incorporated herein by reference in its entirety.

STATEMENT REGARDING FEDERALLY SPONSORED RESEARCH & DEVELOPMENT

This invention was made with government support under 20-CRHF-0-6055 awarded by the USDA/NIFA. The government has certain rights in the invention.

FIELD OF THE DISCLOSURE

The present disclosure is related to methods of making phage libraries, and in particular, unbiased phage libraries.

BACKGROUND

Phages (also called bacteriophages) are potent tools that can be used for many applications including editing microbial communities including the human microbiome, as biocontrol for foodborne pathogens, and as alternative treatments for antibiotic-resistant bacteria. Central to their natural and applied roles is the ability of phages to infect and efficiently kill targeted host bacteria. Unlocking the potential of phages relies on finding suitable variants that are superior to natural phages, but traditional tools for creating phage variants rely on isolation of individual mutants or inefficient homologous recombination.

The predominant factor governing phage activity and host range is the interaction of a phage with its bacterial receptors. This interaction is primarily mediated by the receptor binding proteins (RBP) of the phage. RBPs can be found in different regions of the phage that may come in contact with the host including the tail fiber (*E. coli* phages T7, T4), baseplate (*Lactococcus* phage TP901-1), tail spikes (*Bacillus* phage SPP1) or capsid filament (*Salmonella* phage phiChi13). RBPs enable phages to adsorb to diverse cell surface molecules including proteins, polysaccharides, lipopolysaccharides and carbohydrate-binding moieties. Phages show high functional plasticity to modulate activity and host range to existing and new hosts under different environments using RBPs. The functional potential of RBPs is highlighted by examples of RBP mutations that make *Yersinia* phage to infect *E. coli*, increase virulence of *Mycobacterium* phage by 1000-fold, or enable phage λ to dynamically adapt to a different receptor Existing methods for creating phage variants such as RBPS variants are laborious, difficult to interpret and are not suitable to high-throughput screening. For example, random mutagenesis screenings are slow, and, critically, generate many variants having multiple mutations, which makes it very difficult to deconvolve the individual effects of each mutation. For another example, "directed evolution" enriches only a small group of phage variants that is biased towards variants that can grow and survive better on the host used to create the phages, resulting in heavily skewed populations of phages. The shortcomings of these traditional processes have hampered phage research.

Meeting this challenge, described herein is a new deep mutational screening method known as Optimized Recombination, Accumulation and Library Expression ("ORACLE") for producing large, unbiased phage libraries. ORACLE is a high-throughput method for producing, enriching, and isolating numerous mutant variants in large quantities. The ORACLE method applied herein, and products generated therefrom, will satisfy a substantial unmet need for rapid screening of phage mutants, which will significantly aid in the production of phage libraries.

BRIEF SUMMARY

In one aspect, the method of preparing an unbiased phage library comprises preparing a population of acceptor phages having a genome comprising recombination sites by providing a base population of lytic phages having a lytic phage genome, removing an endogenous target gene from the lytic phage genome, and inserting the recombination sites into the lytic phage genome; recombining a mutated target gene into a portion of the population of acceptor phages by replicating the population of acceptor phages within a first host bacteria, the first host bacteria comprising a first helper plasmid and a recombination plasmid, wherein the first helper plasmid expresses the endogenous target gene, and the recombination plasmid comprises the mutated target gene and complimentary recombination sites and expresses a recombinase, wherein the recombining produces a mixed phage population comprising acceptor phages and recombined phages, wherein the recombined phages comprise the mutated target gene in their genomes; selectively accumulating the recombined phages from the mixed phage population by replicating the mixed phage population within a second host bacteria, the second host bacteria comprising a second helper plasmid and a counterselection system, wherein the second helper plasmid expresses the endogenous target gene, wherein the counterselection system suppresses replication of the acceptor phages, and wherein replication of acceptor phages is suppressed and replication of recombined phages is amplified to provide a population of accumulated recombined phages, and replicating the population of accumulated recombined phage within a third host bacteria, without a helper plasmid, to provide the unbiased phage library, wherein the lytic phage lyses the first, second and third bacteria.

In another aspect, the invention comprises a product of the above-described process.

BRIEF DESCRIPTION OF THE DRAWINGS

The above-described and other features will be appreciated and understood by those skilled in the art from the following detailed description, drawings, and appended claims.

DETAILED DESCRIPTION

Figure 1:
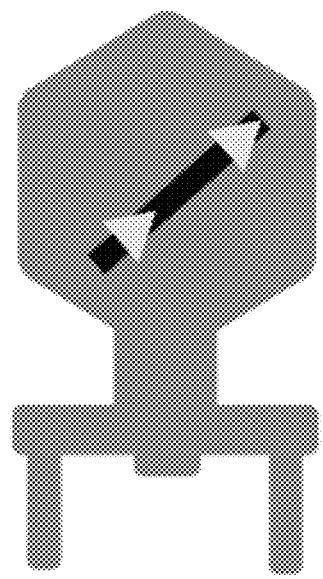
FIG. 1 depicts an illustration of an acceptor phage virion having a recombinant site on its genome.

Unbiased phage libraries are used for many applications including editing microbial communities, as biocontrol for foodborne pathogens, and as alternative treatments for antibiotic-resistant bacteria. Current phage library production methods are limited to a single or small number of mutants and there are currently no high throughput or large library approaches for preparing large unbiased phage libraries. Thus, with current methods, it is not possible to sample the diversity of natural phage populations. Also, the sequence function relationships in phages cannot be narrowly defined. The inventors faced several challenges in developing the methods described herein, including but not limited to, inserting library genes into any phage, preventing bias in the library, and enriching the library over wildtype.

Described herein is deep mutational scanning (DMS), a high-throughput technique, of the tip domain of the T7 phage RBP (tail fiber) to uncover molecular determinants of activity and host range. The tip domain is the distal region of the tail fiber that makes primary contact with the host receptor. ORACLE, a high-throughput, locus-specific, phage genome engineering method was developed to create a large, unbiased library of phage variants at a targeted gene locus. As an example of the ORACLE method, the inventors systematically and comprehensively mutated the tip domain by making all single amino acid substitutions at every site (1660 variants) and quantified the functional role of all variants on multiple bacterial hosts. High resolution functional maps were generated delineating regions concentrated with function-enhancing mutations and host-specific differences in mutational patterns suggesting orientational bias in receptor engagement and exquisite adaptation to individual hosts. However, variants highly adapted to one host perform poorly on others underscoring the tradeoff between activity and host range. Furthermore, the functional potential of RBP was demonstrated by discovering gain-of-function variants against resistant hosts and host-constriction variants that can selectively eliminate certain hosts. To demonstrate therapeutic value of ORACLE, T7 variants were engineered that avert emergence of spontaneous resistance in pathogenic E. coli causing urinary tract infection. The studies described herein demonstrate the molecular drivers of adaptability of the tip domain and identify key functional regions determining activity and host range.

Thus, described herein is a large scale systematic and comprehensive characterization of sequence-function relationship in phages. ORACLE can be applied to other phages and genes to systematically demystify the molecular basis of evolutionary longevity of the most abundant life form on earth.

Advantageously, a large unbiased library as described herein can enable broad sampling of a natural phage population and enables narrowly defined sequence function relationships in phages. In addition, the large unbiased phage library allows one to comprehensively evaluate host range, phage stability, evading anti-phage mechanisms, and characterization of metagenomics parts. In order to overcome the problems of prior methods, the inventors have used a combination of engineered acceptor phages, helper plasmid expression of the wildtype gene, and counterselection (e.g., Cas9) to provide large, unbiased phage libraries.

The method described herein is the ORACLE Method—Optimized Recombination Accumulation Library Expression. The unbiased phage libraries produced by the methods described herein provide for a large population of proportionally equivalent unique phage variants.

Figure 5:
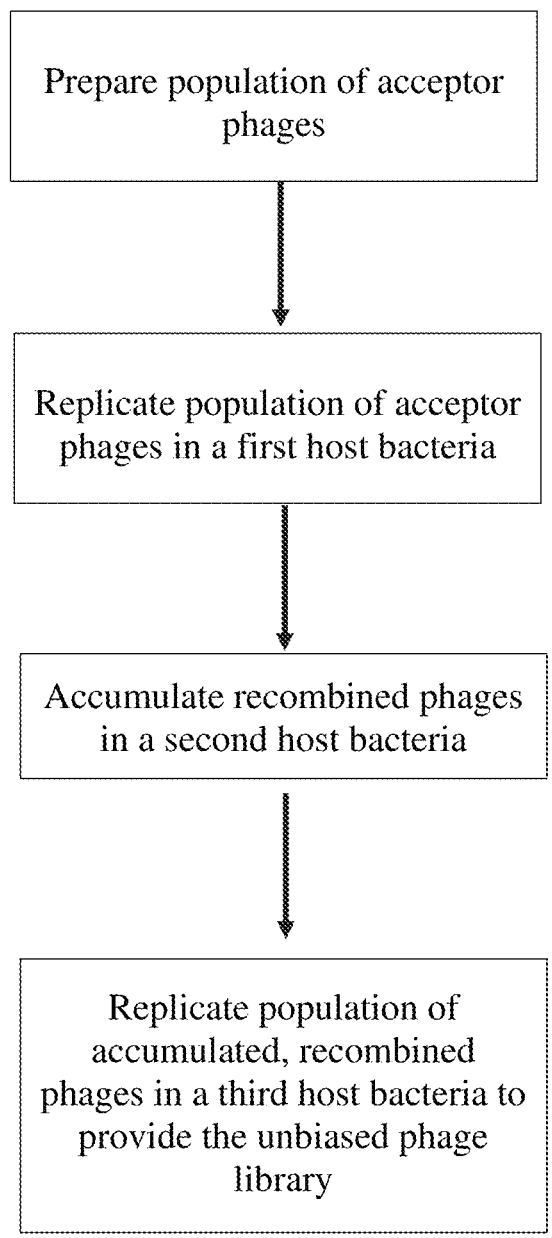
FIG. 5 depicts a block diagram outlining the steps of the method described herein.
Figure 6:
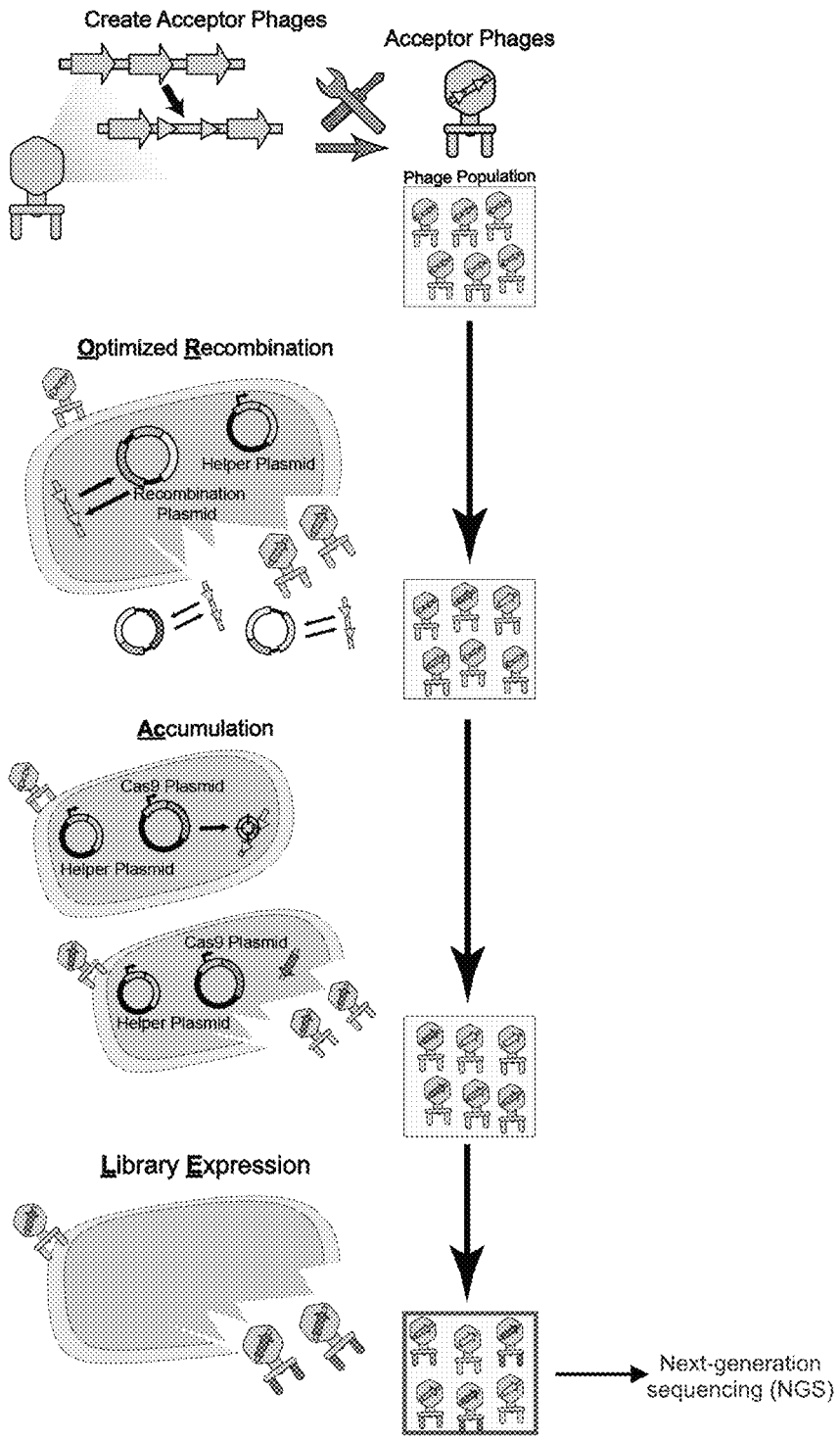
FIG. 6 is a schematic illustration of the four steps of ORACLE: creation of acceptor phage, inserting gene variants (Optimized Recombination), enriching recombined phages (Accumulation) and expressing library for selection (Library Expression).

The "ORACLE" method described herein comprises four phases: (a) making of an acceptor phage; (b) inserting gene variants into the acceptor phage genomes; (c) enriching the recombined phages; and (d) expressing the library for selection. The "acceptor phage" is a phage comprising a synthetic genome wherein the target gene of interest (e.g., tail fiber) is flanked by recombinase sites, which serve as a "landing pad" for insertion variants. One exemplary suitable phage species for "acceptor phage" purposes is phage T7. The steps of the ORACLE method are illustrated in FIGS. 5 and 6.

In the first or Optimized Recombination step, a population of acceptor phages is produced, and a mutated target gene is introduced into the population of acceptor phages. Acceptor phages having a genome comprising recombination sites are prepared by providing a base population of lytic phages having a lytic phage genome, removing an endogenous target gene from the lytic phage genome, and inserting the recombination sites into the lytic phage genome. Thus, instead of the target endogenous gene, the acceptor phages have recombination sites in their genome. The benefit of such acceptor phages includes avoiding transformation and removing the wild type background, ease of creation and ease of growth. A cartoon of an acceptor phage comprising recombination sites (arrows) and having the endogenous gene removed (black bar) is shown in FIG. 1.

In general, lytic phages are very species-specific with regard to their hosts and typically infect a single, bacterial species, or even specific strains within a species. Exemplary lytic phages that infect *E. coli* include phiX174, T1, T2, T3, T4, T5, T6 and T7 bacteriophages. Sb-1 and Pyo phages infect *S. aureus* including methicillin-resistant *Staphylococcus aureus* (MRSA) strains. Dp-1 and Cp-1 are lytic bacteriophages for *S. pneumoniae*. Phage HEf13 infects *Enterococcus faecalis*. CP26F and CP390 are lytic bacteriophage for *Clostridium* species. LL-H is a bacteriophage specific for *Lactobacillus* species. PM16 is specific for *Proteus* species. PaP1 and PADP4 infect *Pseudomonas* species. Phage SPP1 is specific for *Bacillus* species. Phages phiChi13, S16, and E1 are specific for *Salmonella*. Phages AP205, Fri1, and PD6A3 are specific for *Acinetobacter* species. Phages phiYeO3-12 and YpsP-PST are specific for *Yersina* species. Other phages have been identified that infect *Mycobacterium*.

In an aspect, wherein the first, second and third bacteria are *E. coli*, and the base lytic phage comprises phiX174, T1, T2, T3, T4, T5, T6 or T7 phage; wherein the first, second and third bacteria are *Salmonella* sp. and the base lytic phage comprises phiChi13, S16 or E1, wherein the first, second and third bacteria are *Yersinia* sp. and the base lytic phage comprises phiYeO3-12 or YpsP-PST; or wherein the first, second and third bacteria are *Acinetobacter* sp. and the base lytic phage comprises AP205, Fri1 or PD6A3.

In another aspect, the target gene of the method described herein is a gene associated with phage efficacy, host specificity, phage stability, disruption of biofilms, delivery of genetic markers, host resistance, editing of microbial communities (e.g., gut microbiota), timed lysis, biocontrol of foodborne pathogens, and/or antibiotic-resistant bacteria.

The use of lytic phages in the method is important because recombination pre-lysis is an important feature of the method, as will be seen below. The lytic phage lyses the first, second and third bacteria as used in the methods below.

The acceptor phage genome may comprise any suitable recombinase mediated cassette exchange, or RMCE, system known in the art. Any recombinase that can insert a defined piece of dsDNA into a defined site on the phage genome can be used in the methods described herein. Exemplary recombination systems include Cre-loxP, FLP-FRT, R-RS, ΦC31/aat-mediated recombination, D6 recombination (also known as Dre-rox), wherein Cre, FLP and R are bidirectional tyrosine recombinases, and lox, FRT and RS are the respective recognition sequences. In Cre-loxP recombination, for example, the recombination site is a 34 base sequence loxP sequence with an 8 base sequence flanked by symmetric 13 base sequences: ATAACTTCGTATAATGTATGC-TATACGAAGTTAT (SEQ ID NO: 1). The Cre recombinase is well-known in the art. When cells that have loxP sites express the Cre recombinase, a recombination event can occur between loxP sites. The Cre recombinase binds to the first and last 13 base pair regions, forming a dimer. The dimer binds to a dimer on another loxP site to form a tetramer. The double stranded DNA is cut at both loxP sites by the Cre protein, and the strands are rejoined by DNA ligase resulting in a recombination event.

Thus, in an aspect, the genome of the acceptor phage of the method described here may comprises loxP, FRT, ΦC31/aat, RS, or rox recombination sites. In a preferred embodiment, the acceptor phage comprises loxP recombination sites. The genome of the acceptor phage may comprise any suitable recombination system, including improvements and variants on known recombination systems, and including suitable systems as yet unknown in the art.

Figure 2:
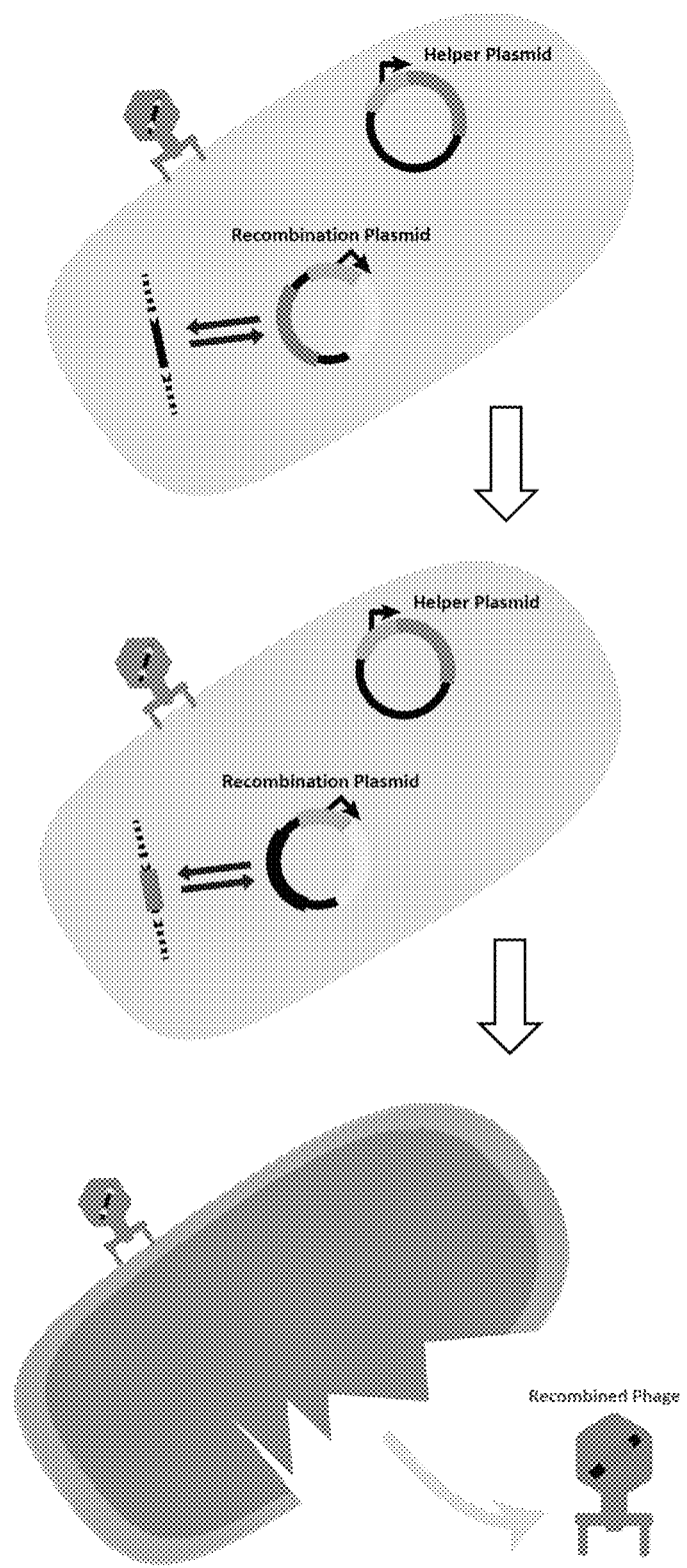
FIG. 2 depicts an illustration of the recombination step of the method described herein.

Also, in the Optimized Recombination step, once the population of acceptor phages is produced, a mutated target gene is recombined into the genome of a portion of the population of acceptor phages. Recombining can comprise replicating the population of acceptor phages with a first host bacteria, the first host bacteria comprising a first helper plasmid and a recombination plasmid. The first helper plasmid expresses the target gene in trans such that even in the absence of the endogenous target gene or for a low activity mutated target gene, all phages can replicate. The recombination plasmid comprises the mutated target gene, and complementary recombination sites and expresses a recombinase, such that upon recombination, a mixed phage population comprising acceptor phages and recombined phages is produced. The recombined phages comprise the mutated target gene in their genomes. A schematic of the recombination step is shown in FIG. 2.

Thus, in the Optimized Recombination step, when the acceptor phages infect a host, they recombine and accept a mutated target gene into their genome. The mutated target gene essentially acts as a donor into a customized phage acceptor. There is a time element associated with this recombination step as the lytic phage are killing the host as they are recombining.

Exemplary first, second and third bacteria comprise, independently, *E. coli, Acinetobacter* species, *Staphylococcus* species, *Enterococcus* species, *Salmonella* species, *Shigella* species, *Streptococcus* species, *Clostridium* species, *Lactobacillus* species, *Neisseria* species, *Proteus* species, *Pseudomonas* species, and *Haemophilus* species.

Preferably, the mutated target gene is a variant library member. For example, a variant library may include a mutation of each position in a target protein sequence of interest to each amino acid. The variant library may include mutations of one or more positions in a genomic locus, a coding region, or a non-coding region. In addition to changes in coding regions, for example, the target gene could be on a non-coding sequence to evaluate transcription rate, for example.

In an aspect, the mutated target gene comprises 1 to 10 substitutions compared to the endogenous target gene. In another aspect, the mutated target gene comprises a domain not found in the endogenous target gene. The domain can encode for 5 to 150 amino acids, or more.

Figure 3:
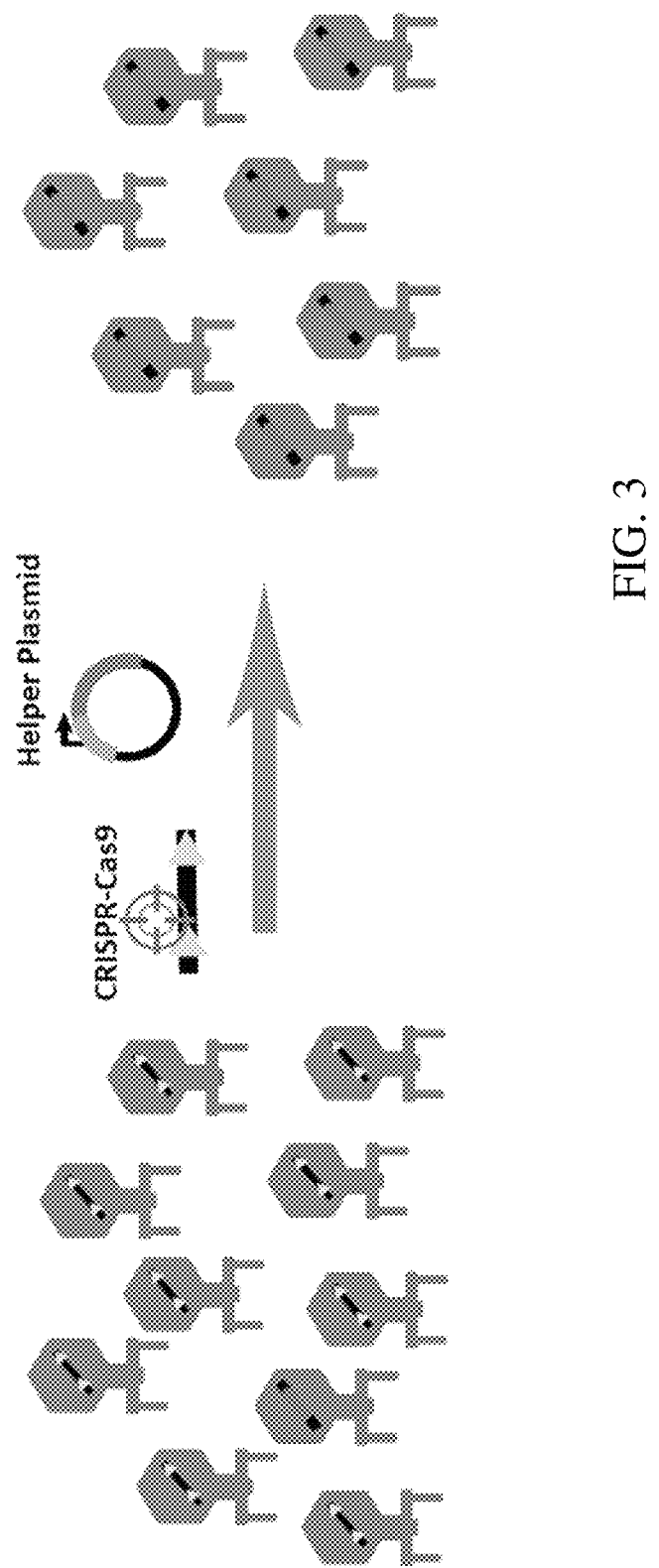
FIG. 3 depicts an illustration of the accumulation step of the method described herein.

The next step in the process is the Accumulation step in which the mixed population of acceptor phages and recombined phages is enriched to remove the unrecombined acceptor phages and enrich the population of recombined phages. Thus, the Accumulation phase comprises selectively accumulating the recombined phages from the mixed phage population by replicating the mixed phage population with a second host bacteria, the second host bacteria comprising a second helper plasmid and a counterselection plasmid, wherein the second helper plasmid expresses the endogenous target gene, wherein the counterselection plasmid suppresses replication of the acceptor phages, and wherein replication of acceptor phages is suppressed and replication of recombined phages is amplified to provide a population of accumulated recombined phages. An embodiment of the accumulation step is shown in FIG. 3.

The first and second host bacteria may be the same or different. Similarly, the first and second helper plasmid may be the same or different so long as the helper plasmid expresses the endogenous target gene.

As used herein, a counterselection plasmid expresses elements for selective cleavage of the genome of the acceptor phages, thus resulting in suppression of replication of the unrecombined acceptor phages.

Figure 4:
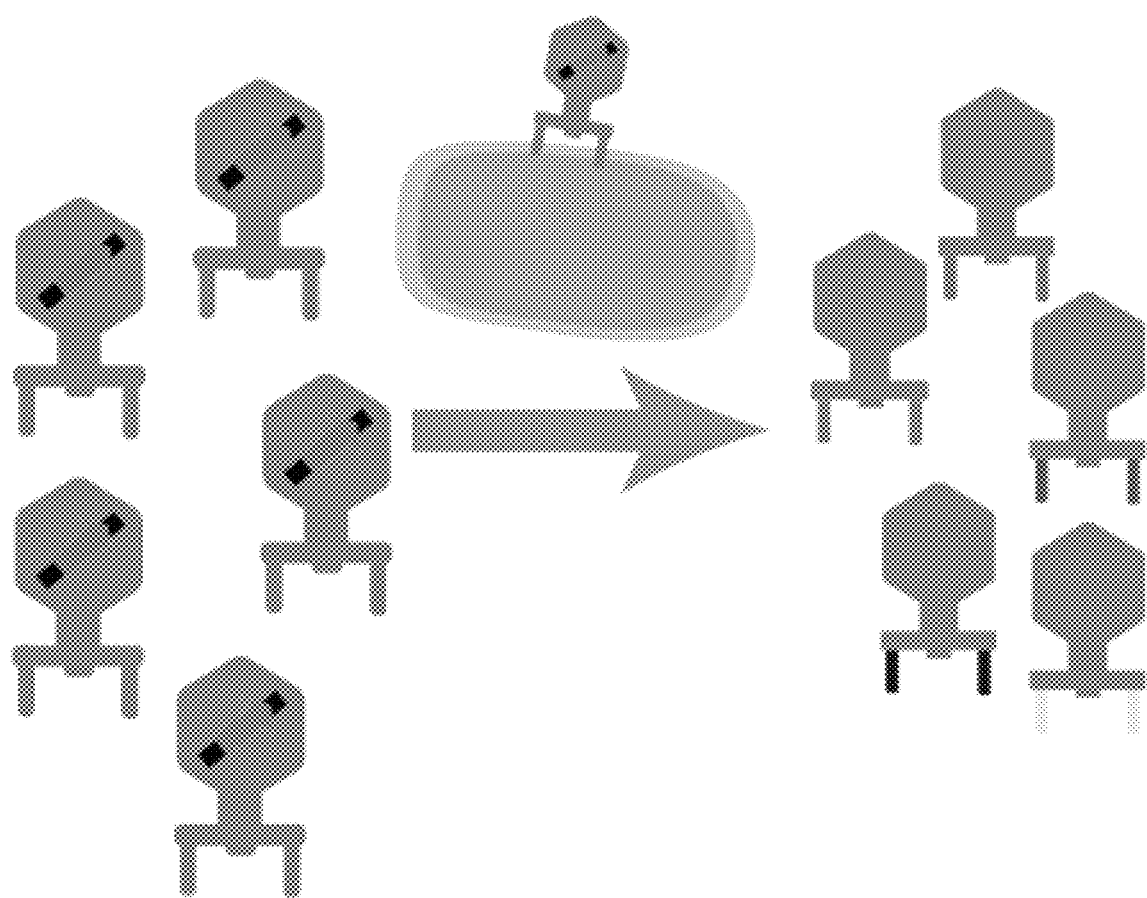
FIG. 4 depicts the library expression step of the method described herein.

Exemplary counterselection plasmids comprise CRISPR-Cas9 plasmids. As shown in FIG. 4, use of a guide RNA (gRNA) targeting the acceptor phages in a CRISPR-Cas9 counterselection strategy compared to a randomized gRNA results in a dramatic accumulation of recombined phages. Besides CRISPR-Cas9, any other site-specific restriction enzyme could be used to accumulate recombined phages.

Thus, in an aspect, the counterselection plasmid comprises CRISPR-Cas9. In a preferred embodiment, the counterselection expresses a guide RNA for the phage genome wildtype gene sequence that is flanked by recombination sites. The counterselection plasmid selects against phage that did not undergo recombination and enriching and accumulating recombined phage variants.

In another aspect, a protective cassette can be included alongside the library gene. In this aspect, the counterselection can comprise restriction modification, phage growth limitation, DISARM, or Ocr from T7 phage. Alternatively, a gene that is toxic to the host can be included in the acceptor. If the acceptor phage does not undergo recombination, the host carrying this acceptor phage could be killed by the toxin encoded in the acceptor.

Critically, during both the recombination phase and the accumulation phase, library bias is prevented by providing the wild type gene in trans on a helper phage, allowing all recombined phage variants to grow with the same efficiency.

In the final Library Expression step, the population of accumulated recombined phages are replicated with a third host bacteria, without a helper plasmid, to provide the unbiased phage library.

The first, second and third host bacteria can be the same or different.

The method can further comprise genomic sequencing of the unbiased phage library.

As a proof of concept, a library of T7 phages with altered tail fibers suitable for high throughput screening and deep mutational scanning has been produced as explained in the Examples and illustrated in FIG. 4. Next Generation Illumina® sequencing has shown that this library remains unbiased throughout creation, demonstrating the effectiveness of this method.

In an aspect, the method further comprises sequencing the mutated target gene in the unbiased phage library.

One advantage of the large, unbiased phage libraries described herein is that deep mutational scans can be performed without a preference for better growing phages over poor growing phages.

The invention described herein also comprises the recombined phage variants produced by the method described herein. In an aspect, the recombined phage variants include recombinase sites flanking the mutated target gene.

The invention is further illustrated by the following non-limiting examples.

EXAMPLES

A library of phage T7 variants was developed according the method described herein. The library comprised 1,660 variants, one for each amino acid substitution available on the T7 RBP tail fiber tip domain. Each variant was then tested in various bacterial hosts to investigate function, as described in detail in the various examples below.

Materials and Methods

Experimental Model and Subject Details
Microbes and Culture Conditions

T7 bacteriophage was obtained from ATCC (ATCC® BAA-1025-B2, NC_001604). *Saccharomyces cerevisiae* BY4741, *Escherichia coli* BW25113 and BL21 are lab stocks, *E. coli* 10G is a highly competent DH10B derivative obtained from Lucigen (60107-1). BW25113ΔrfaD and BW25113ΔrfaG were obtained from Doug Weibel (University of Wisconsin, Madison) and are derived from the Keio collection. UT1473 was obtained from Rod Welch (University of Wisconsin, Madison) and originates from a UTI collection.

All bacterial hosts are grown in and plated on Lb media (1% Tryptone, 0.5% Yeast Extract, 1% NaCl in $dH_2O$, plates additionally contain 1.5% agar, while top agar contains only 0.5% agar) and Lb media was used for all experimentation. Kanamycin (50 μg/ml final concentration, marker for pVRT7Helper1) and spectinomycin (115 μg/ml final concentration, marker for pVRRec1, pVRRec1-Lib and pVRCas9 and derivatives) was added as needed. All incubations of bacterial cultures were performed at 37° C., with liquid cultures shaking at 200-250 rpm unless otherwise specified. Bacterial hosts were streaked on appropriate Lb plates and stored at 4° C.

*S. cerevisiae* BY4741 was grown on YPD (2% peptone, 1% yeast extract, 2% glucose in dH2O, plates additionally contain 2.4% agar), after YAC transformation *S. cerevisiae* BY4741 was grown on SD-Leu (0.17% yeast nitrogen base, 0.5% ammonium sulfate, 0.162% amino acids—Leucine [Sigma Y1376], 2% glucose in dH$_2$O, plates additionally contain 2% agar). All incubations of *S. cerevisiae* were performed at 30° C., with liquid cultures shaking at 200-250 rpm. *S. cerevisiae* BY4741 was streaked on YPD or SD-Leu plates as appropriate and stored at 4° C.

T7 bacteriophage was propagated using *E. coli* BL21 after initial receipt from ATCC and then as described on various hosts in methods. All phage experiments were performing using Lb and culture conditions as described for bacterial hosts. Phages were stored in Lb at 4° C.

For long term storage all microbes were stored as liquid samples at −80° C. in 10% glycerol, 90% relevant media. SOC (2% tryptone, 0.5% yeast extract, 0.2% 5M NaCl, 0.25% 1M KCL, 1% 1M MgCl$_2$, 1% 1M MgSO$_4$, 2% 1M glucose in dH$_2$O) was used to recover host and phages after transformation.

Microbe Authentication: No microbes were specifically authenticated outside of experimental conditions, but T7 phage were cloned extensively (see acceptor phages), partially sequenced, lysed specific hosts and then used for deep sequencing, strongly indicating authenticity. Likewise, bacterial hosts used for DMS were lysed by T7 and cultures were completely clear, indicating no growing strain contamination, and BW25113ΔrfaD and BW25113ΔrfaG deletions have been previously confirmed by sequencing and grow under selection. *S. cerevisiae* BY4741 had no cell authentication but was used only as a cloning host. UTI473 has not been sequenced and has no additional cell authentication.

Method Details
General Cloning

PCR was performed using KAPA HiFi (Roche KK2101) for all experiments with the exception of multiplex PCR for screening Yeast Artificial Chromosomes (YACs), which was performed using KAPA2G Robust PCR kits (Roche KK5005). Golden Gate assembly was performed using New England Biosciences (NEB®) Golden Gate Assembly Kit (BsaI-HFv2, E1601L). Restriction enzymes were purchased from NEB® with the exception of DNAse I (Roche 4716728001). DNA purification was performed using EZNA® Cycle Pure Kits (Omega Bio-tek D6492-01) using the centrifugation protocol. YAC extraction was performed using YeaStarrm Genomic DNA Extraction kits (Zymo Research D2002). Gibson assembly was performed according to the Gibson Assembly Protocol (NEB® E5510) but Gibson Assembly Master Mix was made in lab (final concentration 100 mM Tris-HCL pH 7.5, 20 mM MgCl$_2$, 0.2 mM dATP, 0.2 mM dCTP, 0.2 mM dGTP, 10 mM dTT, 5% PEG-8000, 1 mM NAD+, 4 U/ml T5 exonuclease, 4 U/μl Taq DNA Ligase, 25 U/mL Phusion® polymerase). All cloning was performed according to manufacturer instructions except where noted in methods. If instructions were variable and/or specific conditions are relevant for reproducing results, those conditions are also noted in the relevant methods section.

PCR reactions use 1 μl of approximately 1 ng/μl plasmid or approximately 0.1 ng/μl DNA fragment as template for relevant reactions. PCR reactions using phage as template use 1 μl of undiluted or 1:10 diluted phage stock, genomic extraction was unnecessary. Phage template was initially treated at 65° C. for 10 minutes (for YAC cloning), but we later simply extended the 95° C. denaturation step to 5 minutes (for deep sequencing).

DpnI digest was performed on all PCR that used plasmid as template. Digestion was performed directly on PCR product immediately before purification by combining 1-2 μl DpnI (20-40 units), 5 μl 10× CutSmart® Buffer, PCR product, and dH$_2$O to 50 μl, incubating at 37° C. for 2 hours then heat inactivating at 80° C. for 20 minutes.

DNAse treatment of phages was performed by adding 5 μl undiluted phages, 2 μl 10× DNAse I buffer, 1 μl of 2 U/μl DNAse I, dH$_2$O to 20 μl, then incubating for 20 minutes at 37° C., followed by heat inactivation at 75° C. for 10 minutes. 1 μl of this reaction was used as template for relevant PCR.

Electroporation of plasmids and YACs was performed using a Bio-rad MicroPulser™ (165-2100), Ec2 setting (2 mm cuvette, 2.5 kV, 1 pulse) using 25-50 μl competent cells and 1-2 μl DNA for transformation. Electroporated cells were immediately recovered with 950 μl SOC, then incubated at 37° C. for 1 to 1.5 hours and plated on relevant media.

*E. coli* 10G competent cells were made by adding 8 mL overnight 10G cells to 192 mL SOC (with antibiotics as necessary) and incubating overnight at 21° C. and 200 rpm until approximately OD$_{600}$ of 0.4. Cells were centrifuged at 4° C., 800 g-1000 g for 20 minutes, the supernatant is discarded, and cells are resuspended in 50 mL 10% glycerol. Centrifugation and washing were repeated three times, then cells were resuspended in a final volume of approximately 1 mL 10% glycerol and aliquoted and stored at −80° C. Cells were competent for plasmid and YACs.

Site Directed Mutagenesis (SDM) was performed, in brief, using complementary primers with the desired mutation in the middle of the primer, using 16× cycles of PCR, followed by DpnI digestion and electroporation into competent *E. coli* 10G. Splicing by Overlap Extension (SOE, also known as PCR overlap extension) was performed, in brief, using equimolar ratios of fragments, 16× cycles of PCR using extension based on the combined length of fragments, then a second PCR reaction using 1/100 or 1/1000 diluted product of the first reaction using typical instructions and 5' and 3' end primers for each fragment.

Plasmid Construction and Descriptions pVRT7Helper1 contains a pBR backbone, kanamycin resistance cassette, mCherry, and the T7 tail fiber gp17. Both mCherry and gp17 are under constitutive expression. Gp17 was combined with promoter apFAB47 using SOE and the plasmid assembled by Gibson assembly. After assembly there was a single nucleotide deletion in the promoter. This plasmid is used during optimized recombination and during accumulation in ORACLE to prevent library bias and depletion of variants that grow poorly on *E. coli* 10G.

pVRRec1 contains an SC101 backbone, Cre recombinase, a spectinomycin resistance cassette, and the T7 tail fiber gp17 flanked by Cre lox66 sites with an m2 spacer, a 3' pad region and lox71 sites with a wt spacer (data not shown). Cre recombinase is under constitutive expression. This plasmid was assembled with sequential PCR and Gibson assembly. During assembly we used PCR overhangs and SDM to create two synonymous substitutions in gp16 to remove two BsaI restriction sites to facilitate downstream golden gate assembly. This plasmid was used in recombination assays, as it allows for recombination of wildtype gp17, and is used as template to generate the DMS library. The DMS library pool is referred to as bpVRRec1-Lib and is used during optimized recombination in ORACLE.

pVRCas9 contains an SC101 backbone, a spectinomycin resistance cassette and cas9 cassette capable of ready BsaI cloning of gRNA. This plasmid is used directly as part of the negative control for the accumulation assay, and has five derivatives, pVRCas9-1 through -5, each with a different gRNA targeting the fixed region in the T7 acceptor phage. pVRCas9 was created with Gibson assembly, while derivatives were assembled by phosphorylation and annealing gRNA oligos (100 µM forward and reverse oligo, 5 µl T4 Ligase buffer, 1 µl T4 PNK, to 50 µl dH$_2$O, incubate at 37° C. for 1 hour, 96° C. for 6 minutes then 0.1 C/s temperature reduction to 23° C.), then Golden Gate cloning (1 µl annealed oligo, 75 ng pVRCas9, 2 µl T4 DNA Ligase Buffer, 1 µl Golden Gate Enzyme Mix, dH$_2$O to 20 µl. Incubation at 37° C. for 1 hour then 60° C. for 5 minutes, followed by direct transformation of 1 µl, plated on Lb with spectinomycin). Note pVRCas9-3 was the most inhibitory (data not shown) and was the only plasmid used in accumulation during ORACLE. All plasmid backbones and gene fragments are lab stocks.

Bacterial Growth Phases and Calculation of Concentration

Bacterial concentrations were determined by serial dilution of bacterial culture and subsequent plating and bead spreading of 100 µl of a countable dilution (targeting 50 CFU) on Lb plates. Plates were incubated overnight and counted the next morning. Typically, two to three dilution series were performed for each host to initially establish concentration at different $OD_{600}$ and subsequent concentrations were confirmed with a single dilution series for later experiments.

Stationary phase cultures are created by growing bacteria overnight (totaling approximately 20-30 hours of incubation) at 37° C. Cultures are briefly vortexed then used directly. Exponential phase culture consists of stationary culture diluted 1:20 in Lb then incubated at 37° C. until an $OD_{600}$ of ~0.4-0.8 is reached, typically 40 minutes to 1 hour and 20 minutes depending on the strain and antibiotic, after which cultures are briefly vortexed and used directly.

Phage Purification, Titering, Efficiency of Plating (EOP) Assays and Multiplicity of Infection (MOI) Calculation Phage lysate was purified by centrifuging phage lysate at 16 g, then filtering supernatant through a 0.22 µM filter. Chloroform was not routinely used unless destruction of any remaining host was considered necessary and is mentioned in such cases.

To establish titer, phage samples were typically serially diluted (1:10 or 1:100 dilutions made to 1 mL in 1.5 microcentrifuge tubes) in Lb to a $10^{-8}$ dilution for preliminary titering by spot assay. Spot assays were performed by mixing 250 µl of relevant bacterial host in stationary phase with 3.5 mL of 0.5% top agar, briefly vortexing, then plating on Lb plates warmed to 37° C. After plates solidified (typically approximately 5 minutes), 1.5 µl of each dilution of phage sample was spotted in series on the plate. Plates were incubated and checked at 2-4 hours and overnight (approximately 20-30 hours) to establish a preliminary titer.

After a preliminary titer was established, phage samples were serially diluted in triplicate for efficiency of plating (EOP) assays. EOP assays were performed using whole plates instead of spot plates to avoid inaccurate interpretation of results due to spotting error. To perform the whole plate EOP assay, 250 µl of bacterial host in stationary or exponential phase was mixed with between 5 to 50 µl of phages from a relevant dilution targeted to obtain 50 plaque forming units (PFUs) after overnight incubation. The phage and host mixture was briefly vortexed, briefly centrifuged, then added to 3.5 mL of 0.5% top agar, which was again briefly vortexed and immediately plated on Lb plates warmed to 37° C. After plates solidified (typically approximately 5 minutes), plates were inverted and incubated overnight. PFUs were typically counted at 4-6 hours and after overnight incubation (approximately 20-30 hours) and the total overnight PFU count used to establish titer of the phage sample. PFU totals between 10 and 300 PFU were typically considered acceptable, otherwise plating was repeated for the same dilution series. This was repeated in triplicate for each phage sample on each relevant host to establish phage titer.

EOP was determined using a reference host, typically *E. coli* 10G with pVRT7Helper1. EOP values were generated for each of the three dilutions by taking the phage titer on the test host divided by the phage titer on the reference host, and this value was subsequently $log_{10}$ transformed. Values are reported as mean±SD.

MOI was calculated by dividing phage titer by bacterial concentration. MOI for the T7 variant library after the variant gene is expressed was estimated by titering on 10G with pVRT7Helper1.

Limit of Detection (LOD) for T7 ACC and T7ΔGP17

Both T7 acceptor phages (T7 Acc) and T7 lacking a tail fiber (T7Δgp17) are unable to plaque on host lacking pVRT7Helper1, but phages do express a tail fiber due to propagating on host with pVRT7Helper1. Functionally this allows these phages to complete one infection cycle and kill one host if that host does not also contain pVRT7Helper1. At an MOI of greater than approximately 2 we noted plates no longer form lawns of bacteria but instead contain individual colonies or are clear, reflective of these individual assassinations. As expected, this effect occurs at different concentrations of phages for exponential or stationary host due to different host concentration at those stages of growth. As plaques cannot form under these conditions, and these infections are not productive beyond a single infection, we simply used this cut off as the limit of detection for this assay.

Recombination Rate Assay

To establish recombination rate, we passaged T7 acceptor phages on 5 mL exponential phase *E. coli* 10G containing pVRT7Helper1 and pVRRec1. pVRRec1 was used because the recombined gp17 is wildtype, ensuring every recombined phage is plaque-capable. We sought to evaluate recombination rate after only 1 passage through the host to avoid misinterpretation of results in case recombined phages had different fitness than unrecombined phages. We used an MOI of 10 and allowed passage for 30 minutes, sufficient time for one wildtype phage passage, after which we halted any remaining reactions by adding 200 µl of chloroform and lysing the remaining bacterial host. Phages were then purified to acquire the final phage population.

We established the phage population titer on 10G and 10G with pVRT7Helper1. Both acceptor phages and recombined phages are capable of plaquing on 10G with pVRT7Helper1 and this phage titer is used to count the total phage population. Only recombined phages are capable of plaquing on 10G and this titer is used to count recombined phages. Recombination rate was established as the fraction titer of recombined phages divided by recombined phages. This was repeated in triplicate and reported as mean±SD.

Accumulation Assay

To validate accumulation of recombined phages over acceptor phages we first generated a population of recombined phages using the same scheme as outlined for the recombination rate assay. After recombination this phage population contained primarily T7 acceptor phages with a small percentage of recombined phage containing a wildtype gp17. This phage population was passaged on 10G containing pVRT7Helper1 and either pVRCas9-3 (targeting the fixed region in the acceptor phage) or pVRCas9 (randomized control). Phages were incubated with host in 5 mL total at an initial MOI of 1 based on the titer of the whole phage population. Every 30 minutes until 180 minutes, and thereafter every 60 minutes until 300 minutes, approximately 250 µl of culture was removed, infection was stopped by adding 100 µl of chloroform, and phage samples were purified to establish the phage population at that timepoint. Titer at each timepoint was determined on both 10G and 10G with pVRT7Helper1 with a single dilution series using whole plate plaque assay. Percentage accumulation was derived by dividing titer on 10G by titer on 10G with pVRT7Helper1. Accumulation on both hosts was repeated in triplicate and reported as mean±SD.

Plasmid Library Preparation

To create the DMS variant plasmid library, oligos were first designed and ordered from Agilent as a SurePrint Oligonucleotide Library (Product G7220A, OLS 131-150mers). Every oligo contained a single substitution at a single position in the tip domain, overall including all non-synonymous substitutions, a single synonymous substitution, and a stop codon. We used the most frequently found codon for each amino acid in gp17 to define the codon for each substitution. Oligos contained BsaI sites at each end to facilitate Golden Gate cloning. To accommodate a shorter oligo length the library was split into three pools covering the whole tip domain. Oligo pools were amplified by PCR using 0.005 pmol total oligo pool as template and 15 total cycles to prevent PCR bias, then pools were purified. pVRRec1 was used as template in a PCR reaction to create three backbones for each of the three pools. Backbones were treated with BsaI and Antarctic Phosphatase as follows. 5 µl 10× CutSmart®, 2 µl BsaI, approximately 1177 ng backbone, dH$_2$O to 50 µl was mixed and incubated at 37° C. for 2 hours, after which 1 µl additional BsaI, 2 µl Antartic Phosphatase, 5.89 µl 10× Antartic Phosphatase buffer was spiked into reaction. Reaction was incubated for 1 more hour at 37° C., then enzymes were heat inactivated at 65° C. for 20 minutes (concentration approximately 20 ng/µl at this point) and used directly (no purification) in Golden Gate Assembly. Golden gate assembly was performed using approximately 100 ng of relevant pool backbone and a 2× molar ratio for oligos (approximately 10 ng), combined with 2 µl 10× T4 DNA ligase buffer, 1 µl NEB Golden Gate Enzyme mix and dH$_2$O to 20 µl. These reactions were cycled 37° C. to 16° C. over 5 minutes, 30×, then held at 60° C. for 5 minutes to complete Golden Gate assembly. Membrane drop dialysis was then performed on each library pool for 75 minutes to enhance transformation efficiency. 2 µl of each pool was transformed into 33 µl C3020 DH10B competent cells. Drop plates were made at this point (spotting 2.5 µl of dilutions of each library on Lb plates with spectinomycin) and total actual transformed cells were estimated at approximately 2×10$^5$ CFU/mL. Each 1 mL pool was added to 4 mL Lb with spectinomycin and incubated overnight, then was purified. Plasmids concentration was determined by nanodrop and pools were then combined at an equimolar ratio to create the final phage variant pool, denoted as pVRRec1-Lib. pVRRec1-Lib was transformed into E. coli 10G with pVRT7Helper1. Drop plates were made (spotting 2.5 µl of dilutions of each library onto Lb plates with spectinomycin and kanamycin) and total actual transformed cells were estimated at approximately 2×10$^5$ CFU/mL. The 1 mL library was added to 4 mL Lb with spectinomycin and kanamycin and incubated overnight. This host, E. coli 10G with pVRT7Helper1 and pVRRec1-Lib, was the host used for Optimized Recombination during ORACLE.

Oracle—Engineering T7 Acceptor Phages and Acceptor Phage Considerations

Acceptor phages were assembled using YAC rebooting, which requires yeast transformation of relevant DNA segments, created as follows. A prs315 yeast centromere plasmid was split into three segments by PCR, separating the centromere and leucine selection marker, which partially limits recircularization and improved assembly efficiency. Wild type T7 segments were made by PCR using wildtype T7 as template. At the site of recombination the acceptor phage contains, in order, lox71 sites with an m2 spacer to facilitate one way recombinase mediated cassette exchange (RMCE), a fixed sequence that was derived from sfGFP with a nonsense mutation, a short region mimicking gp17 to allow detection of acceptor phages by deep sequencing, a 3' 'pad' to facilitate deep sequencing, and lox66 sites with a wt spacer (data not shown). This entire region was turned into one DNA segment by serial SOE reactions.

DNA parts were combined together (0.1 pmol/segment) and transformed into S. cerevisiae BY4741 using a high efficiency yeast transformation protocol using SD-Leu selection. After 2-3 days colonies were picked and directly assayed by multiplex colony PCR to assay assembly. Multiplex PCR interrogated junctions in the YAC construct and was an effective way of distinguishing correctly assembled YACs. Correctly assembled YACs were purified and transformed into E. coli 10G cells containing pVRT7Helper1, and after recovery 400 µl was used to inoculate 4.6 mL Lb. This culture was incubated until lysis, after which phages were purified to create the acceptor phage stock.

Oracle—Optimized Recombination

Recombination was performed by adding T7 Acceptor phages (MOI approximately 5) to 15 mL exponential phase 10G with pVRT7Helper1 and pVRRec1-Lib, split across three 5 mL cultures. A high MOI was used to allow for one effective infection cycle. Cultures were incubated until lysis (approximately 30 minutes). Lysed cultures were combined and purified. This phage population constitutes the initial recombined phage population and contained an estimated 2×10$^7$ variants/mL in a total phage population of approximately 2×10$^{10}$ PFU/mL. The remainder of the phages are acceptor phages. Note pVRT7Helper1 ensures progeny should remain viable by providing gp17 in trans.

Oracle—Accumulation

Accumulation was performed by adding approximately MOI of 0.2 of recombined phages (50 µl or approximately 1×10$^9$ total phages) to 5 mL of stationary phase E. coli 10G with pVRT7Hlper1 and pVRCas9-3 resuspended in fresh Lb with kanamycin and spectinomycin. Cultures were incubated until lysis (approximately 3.5 hours), then phages were purified. This MOI was chosen to target 1% of acceptor phages remaining in the final population as an internal control—the remainder of the phage population was accumulated variant phages. Stationary phase was used because it was more inhibitory based on EOP (data not shown). Note pVRT7Helper1 still ensures progeny should remain viable by providing gp17 in trans and progeny from accumulation do not fully express variant genes.

Oracle—Library Expression

Library expression was performed by adding the accumulated DMs library to 5 mL E. coli 10G (with no plasmid) at an MOI of approximately 1. Cultures were incubated for 30 minutes, then 200 µl chloroform was added the culture to lyse any remaining cells and phages purified. This constitutes the final phage variant library with full expression of the variant gp17. This phage population was directly sequenced to establish the pre-selection library population.

DMS Passaging and Selection

Passaging was performed for all bacterial hosts in the same way. The T7 variant library was added to 5 mL of exponential host at an MOI of approximately $10^{-2}$ and the culture was allowed to fully lyse (typically 40 to 80 minutes depending on the host). Phage lysate was purified and then the titer established for the host the phage was being passaged on. This process was then repeated using the passaged phage lysate. An MOI of $10^{-2}$ was chosen to allow phages which grow slower a chance to replicate. For reference under these conditions we expect wild type to complete four infection cycles on a susceptible host. Phage lysate from the second passage was retained and used as template for deep sequencing to establish the post-selection phage population. The entire process was repeated in biological triplicate for each host.

Sample Preparation for Deep Sequencing

We used deep sequencing to evaluate phage populations. We first amplified the tip domain by two step PCR, or tailed amplicon sequencing, using KAPA HiFi™ Primers for deep sequencing attach to constant regions adjacent to the tip domain (the target region is 304 bp total). Constant regions were also installed in the fixed region of the acceptor phages for the same size amplicon so acceptor phages can also be detected. The first PCR reaction adds an internal barcode (used for technical replicates to assay PCR skew), a variable N region (to assist with nucleotide diversity during deep sequencing, this is essential for DMS libraries due to low diversity), and the universal Illumina® adapter. Undiluted phages are used as template. Four forward and four reverse primers were used in each reaction, each with a variable N count (0, 2, 4, or 8). Primers were mixed at equimolar ratios and total primers used was per recommended primer concentration. PCR was performed using 12 total cycles in the first PCR reaction, then the product of this reaction was then purified. The second PCR reaction adds an index and the Illumina® 'stem'. 1 µl of purified product from the first reaction was used as template using 8 total PCR cycles. The product of this reaction was purified and was used directly for deep sequencing. Each phage population was sampled at least twice using separate internal barcodes, and no PCR reactions were pooled. All phage samples were deep sequenced using an Illumina® Miseq® System, 2×250 read length using MiSeq® Reagent Kit v2 or v2 Nano according to vendor documentation.

Deep Sequencing Analysis and Considerations

Paired-end Illumina® sequencing reads were merged with FLASH (Fast Length Adjustment of SHort reads) using the default software parameters. Phred quality scores (Q scores) were used to compute the total number of expected errors (E) for each merged read and reads exceeding an Emax of 1 were removed. Wildtype, acceptor phages, and each variant were then counted in the deep sequencing output. We correlated read counts for each technical replicate to determine if there was any notable skew from PCR or deep sequencing. Replicates correlated extremely well (R=>0.98 for all samples) indicating no relevant PCR skew. Besides wildtype and acceptor counts, we included only single substitutions in our analysis. While this limits the scope of the analysis, it greatly reduced the possibility of deep sequencing error resulting in an incorrect read count for a variant, as virtually every relevant error would result in at least a double substitution in our library. With this in mind, and to avoid missing low abundance members after passaging, we used a low read cutoff of 2 and did not utilize a pseudo-count of 1 for each position.

Of the 1660 variants, three (S487P, L524M and R542N) fell below our limit of detection in the variant pool before selection. These positions were excluded from analysis as a pre-selection population could not be accurately determined, although both S487P and L542M subsequently emerged in several post-selection populations indicating they were present below the limit of detection. Technical replicates of each biological replicate were aggregated, and each biological replicate was correlated to determine reproducibility (data not shown). To score enrichment for each variant we used a basic functional score (F), averaging results of the three biological replicates where $$F = \bar{x} \frac{\text{Variant}\%_{Post-Passage}}{\text{Variant}\%_{Pre-Passage}}.$$

To compare variant performance across hosts we normalized functional score ($F_N$) to wildtype, where $$F_N = \bar{x} \frac{\text{Variant}\%_{Post-Passage}}{\text{Variant}\%_{Pre-Passage}} \bigg/ \frac{WT\%_{Post-Passage}}{WT\%_{Pre-Passage}}.$$

Classifying Variants and Considerations

To define variant behavior on 10G, BL21, and BW25113 we considered variants depleted if $F_N$ was below 0.1 (i.e. performed ten times worse than wild type), tolerated if between 0.1 and 2, and enriched if above 2 (i.e. performed twice as good as wild type). As wildtype T7 effectively grows on all three strains, we reasoned that it would be more challenging for an enriched mutant to surpass wildtype than it would be for a mutant to become depleted. These cutoffs are semi-arbitrary but were supported based on preliminary plaque assay results and the extent of standard deviation across biological replicates. For BW25113ΔrfaD and BW25113ΔrfaG similar logic does not apply because wild type does not grow effectively on these strains (FIG. 20-25). For example, we cannot define substitutions as 'tolerated', because growing comparable to wild type results in depletion on these hosts. As such we simply defined enriched members as performing at least ten times better ($F_N>10$) than wild type, with the prediction that any sustained variants are likely relevant for gain-of-function on these strains.

Figure 17:
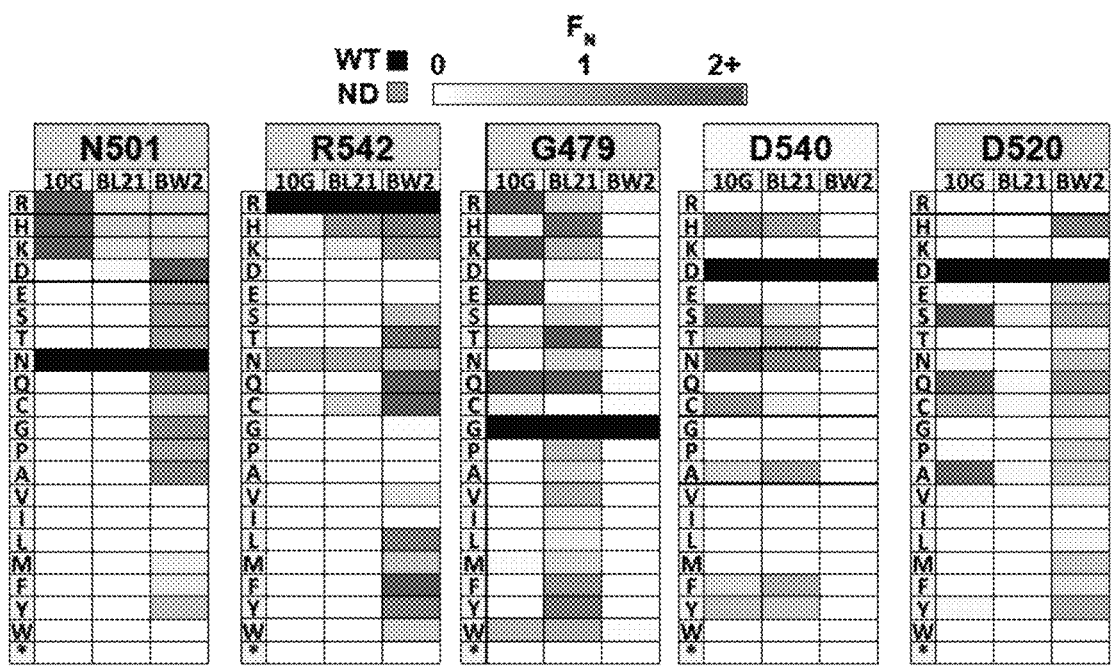
FIG. 17 shows host-specific differences in substitution patterns at five positions in the tip domain recapitulated from FIG. 11.
Figure 18:
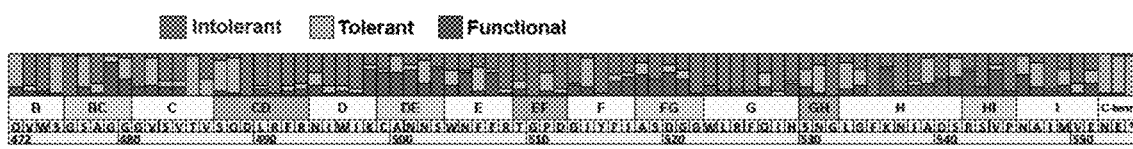
FIG. 18 shows the role of each position determined by aggregating scores of all substitutions in all hosts at that position. Substitutions are classified as intolerant ($F_N<0.1$ in all strains), tolerant ($F_N>0.1$ in all strains), or functional ($F_N<0.1$ in one strain, $F_N>0.1$ in another strain).
Figure 19:
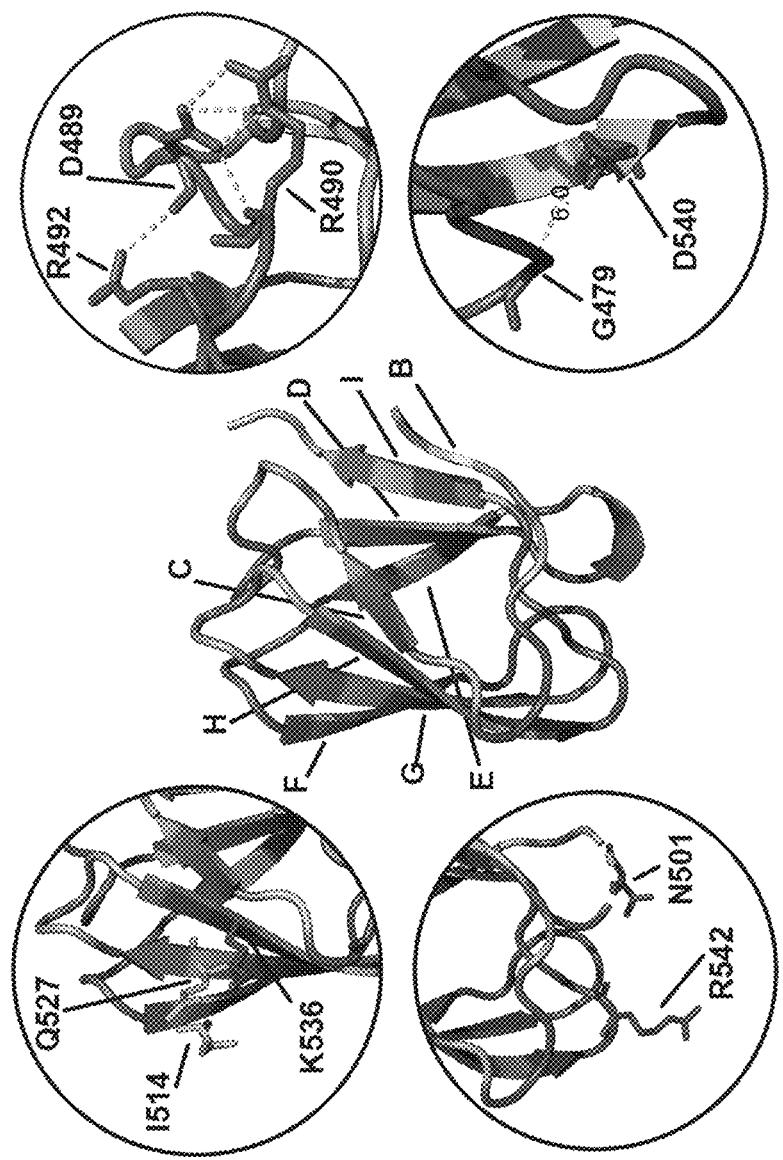
FIG. 19 shows a crystal structure of the tip domain (center) with each residue colored as intolerant, tolerant, or functional based on the dominant effect at that position, β-sheets labeled. Key interactions defining function and orientation are highlighted in peripheral panels.

We compared variant $F_N$ across 10G, BL21 and BW25113 to further characterize each variant and find functional variants (FIG. 17-19). We sought to identify variants that had meaningfully different performance on different strains, which would be strong evidence that either the wild type residue or the variant was important in a host-specific context. In addition to providing direct insight intro structure-function relationships, such substitutions or positions are ideal engineering targets for altering host range or increasing activity in engineered phages. We considered substitutions that were depleted ($F_N<0.1$) on all three hosts to be intolerant, while substitutions that were tolerated or enriched ($F_N>0.1$) in all three hosts to be generally tolerated. Substitutions that were depleted on one host but tolerated or enriched on another were considered functional. To broadly characterize each position, we counted the number of substitutions at that position that fell into each category, and colored positions as functional if over 33% of substitutions at that position were functional, intolerant if over 50% of substitutions were intolerant, and tolerant otherwise. We found these cutoffs to effectively group residues of interest, although we note there remain substitutions that could be tolerant and relevant in different contexts or intolerant for these three hosts but not others.

For defining ideal host constriction mutants (FIG. 29-32) we first constricted $F_N$ values that were greater than 1 to reduce the impact of higher scores on this comparison. Specifically we generated Functional Difference ($F_D$), where if $F_N<1$, $F_D=F_N$, and where $F_N>1$, $$F_D = \frac{F_N - 1}{\max(\text{Strain}F_N) - 1} + 1.$$

$F_D$ thus ranged from 0 to 2 for each substitution where scores above 1 are normalized to the maximum value for that strain and fall between 1 and 2, minimizing but not eliminating weight for enrichment. We reasoned that for the purposes of finding host constriction mutants, the extent of enrichment for a substitution is less relevant than if that substitution did poorly on another host. Put another way, it does not matter if a substitution is tolerated or enriched so long as it is depleted on a different host. For example, V544R has an $F_N$ of 9.09 in *E. coli* 10G but 0.07 in *E. coli* BW25113, while G479E has an $F_N$ of 1.73 in *E. coli* 10G and falls below the limit of detection for *E. coli* BW25113. For host constriction both positions should be scored highly, as the mutations can be tolerated or enriched in one strain but are depleted in another. In contrast A500H has an $F_N$ of 7.46 in *E. coli* 10G and 1.2 in *E. coli* BW25113. While $F_N$ differs significantly and the substitution is enriched on one strain, it is still tolerated in the other strain and thus makes a poor host constriction target. After generating $F_D$ we simply subtracted $F_D$ from each strain (FIG. 29-32). Substitutions for host range constriction were considered ideal if $|F_D|<1$.

Example 1: Oracle Workflow for Creating Phage Variant Libraries

We developed a high-throughput precision phage genome engineering technology called ORACLE (Optimized Recombination, Accumulation and Library Expression) to create large, unbiased library of phage variants to investigate sequence-function relationships in phages. Unfortunately, direct transformation of phage libraries, while ideal for creating one or small groups of synthetic phages, generally will not work because phage genomes are typically too large for library transformation or are reliant on highly transformable hosts. Homologous recombination has low and variable recombination rates and retains high levels of wildtype phage which mask library members. Libraries of lysogenic phages could potentially be made using conventional bacterial genome engineering tools as the phage integrates into the host genome. However, this approach is not applicable to obligate lytic phages. Our desire to develop ORACLE for obligate lytic phages is motivated by their exclusive mandated use for phage therapy. ORACLE solves three key problems. First, transformation bottleneck is eliminated because phage variants are created during the infection cycle. By recombining a donor cassette containing prespecified variants to a targeted site on the phage genome, ORACLE allows sequence programmability and generalizability to virtually any phage. Second, ORACLE minimizes library bias that can rapidly arise due to fitness advantage or deficiency of any variant on the propagating host from exponential phage growth. Minimizing bias is critical because variants that perform poorly on propagating host but well on target host may disappear during propagation. Third, ORACLE prevents extreme abundance of wildtype over variants which allows resolving and scoring even small functional differences between variants. Though designed for obligate lytic phages, ORACLE can be applied to lysogenic phages as well.

Figure 7:
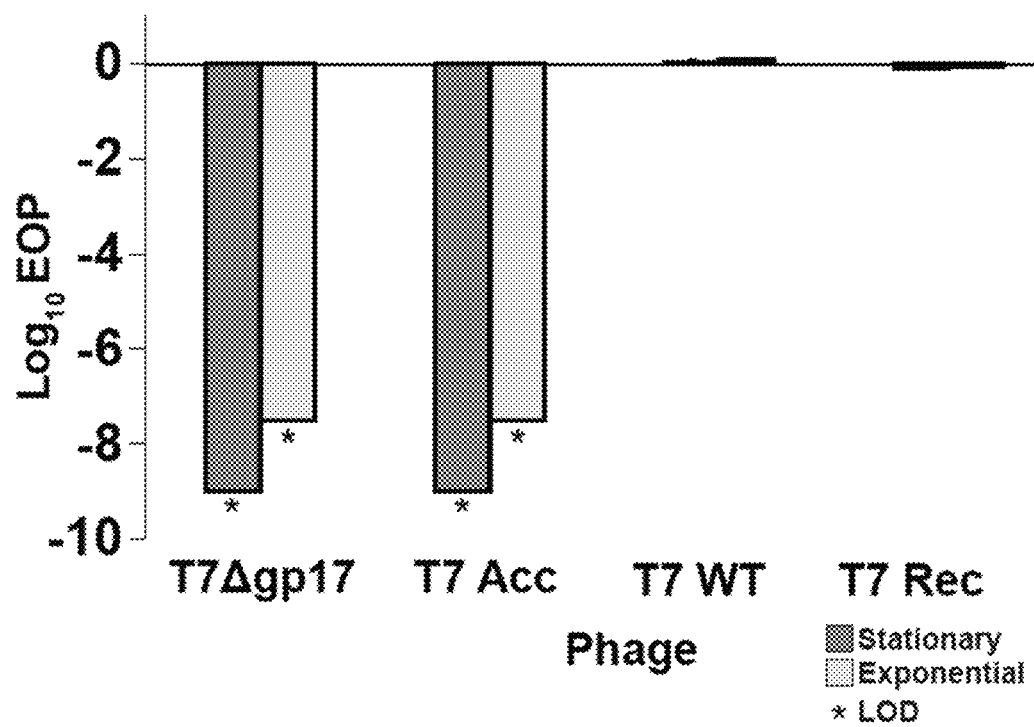
FIG. 7 shows the ability of different versions of T7 to infect E. coli 10G in exponential (dark gray bar) and stationary (light gray bar) phases by EOP using exponential 10G with gp17 helper plasmid as reference host. T7 without tail fiber (T7Δgp17) and T7 without tail fiber (T7Δgp17) plaque poorly, but wildtype T7 (T7 WT), and T7 with gp17 recombined into the acceptor locus (T7 Rec) plaque efficiently. All data represented as mean±SD of biological triplicate.
Figure 8:
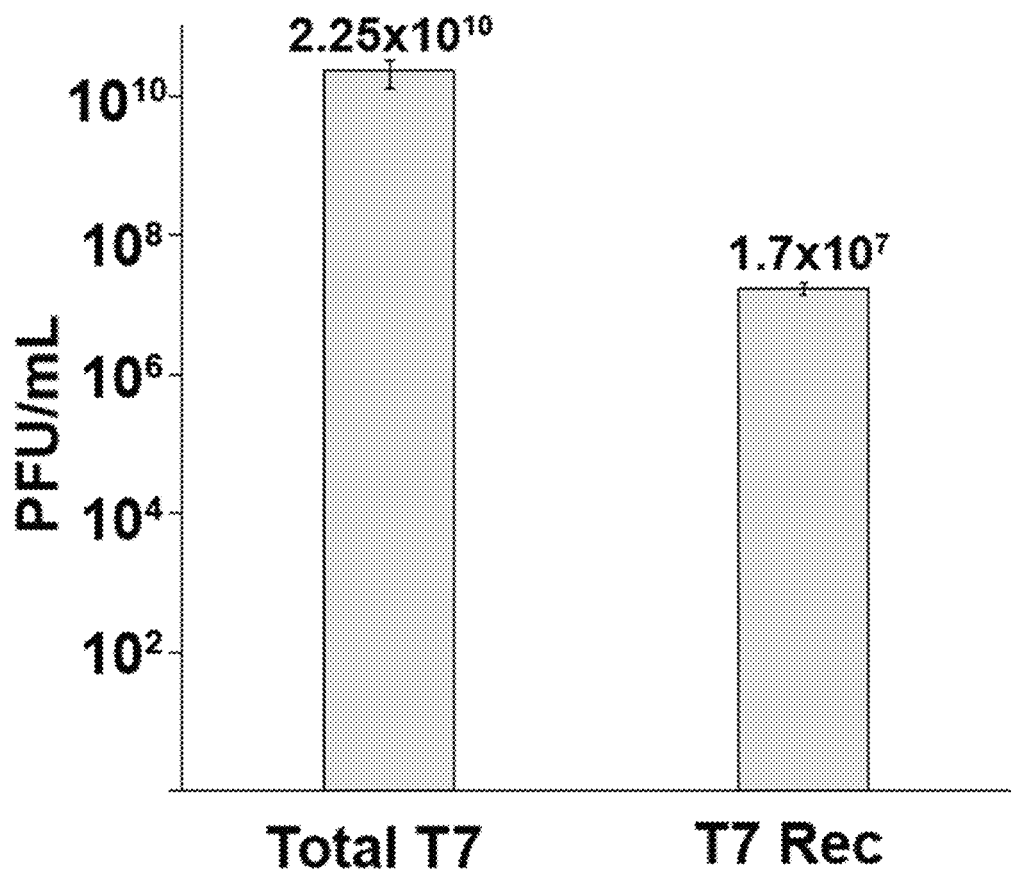
FIG. 8 shows the concentration of total (Total T7) and recombined (T7 Rec) phages after a single passage on host containing Cre recombinase system. Recombination rate is estimated to be approximately $7.19 \times 10^{-4}$.
Figure 9:
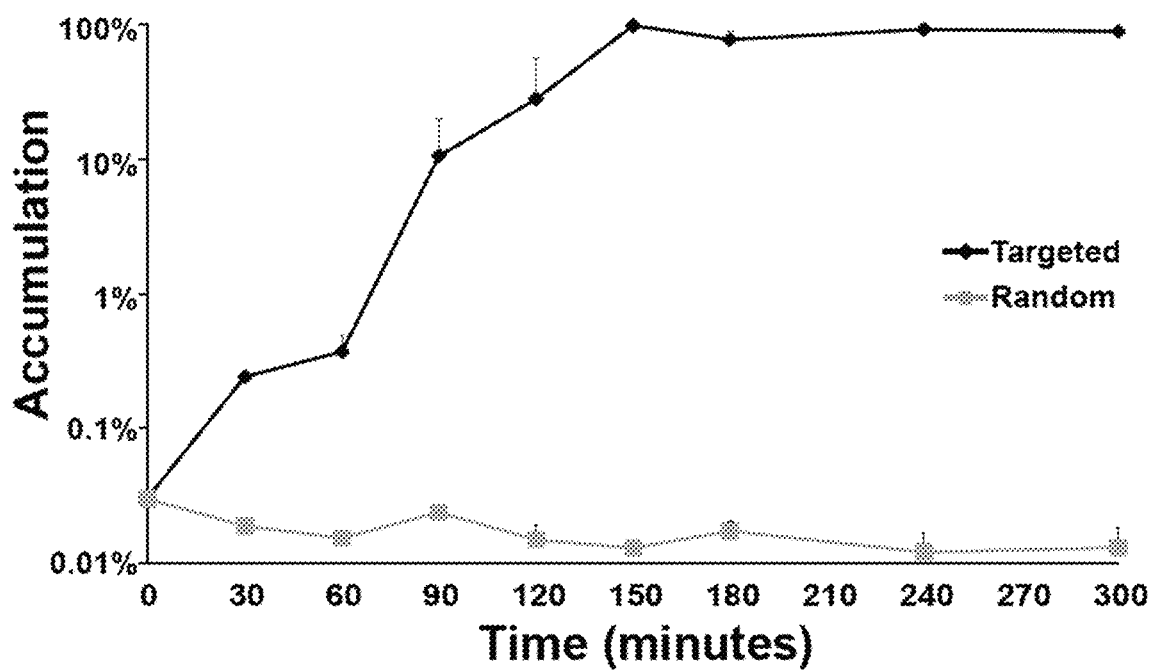
FIG. 9 shows that percentage of recombined phages in total phages when using gRNA targeting fixed sequence at acceptor site T7 Acc (Targeted) or randomized gRNA (Random).
Figure 10:
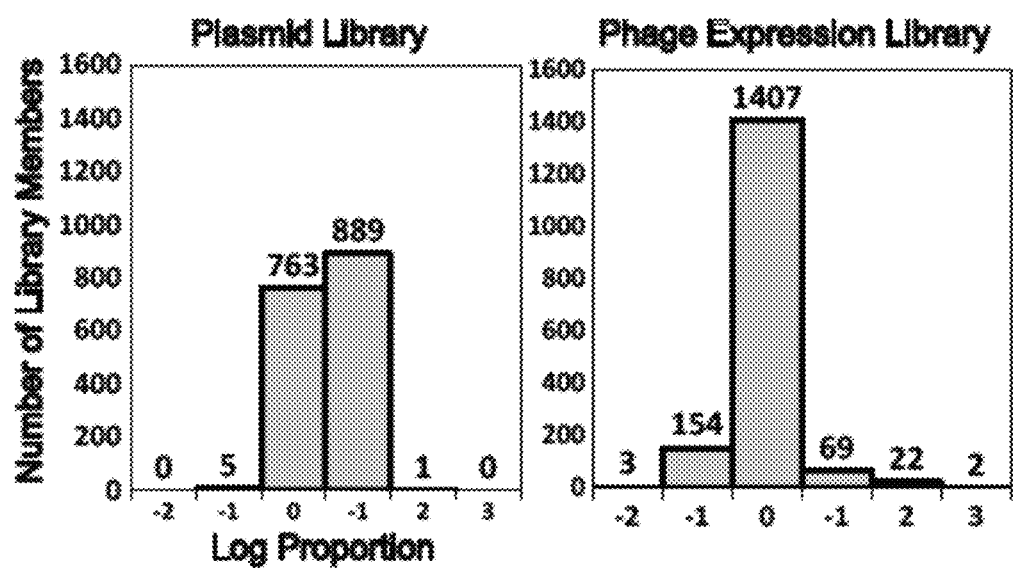
FIG. 10 is a histogram of abundance of variants in the input plasmid library (left) and on the phage genome after ORACLE (right) binned using log proportion centered on equal representation.

ORACLE is carried out in four steps by (a) making acceptor phage, (b) inserting gene variants, (c) enriching recombined phages, and (d) expressing library for selection (FIG. 6). An 'acceptor phage' is a synthetic phage genome where the gene of interest (i.e., tail fiber) is replaced with a fixed sequence flanked by Cre recombinase sites to serve as a landing pad for inserting variants (data not shown). T7 acceptor phages lacking a wildtype tail fiber gene cannot plaque on *E. coli* and do not spontaneously re-acquire the tail fiber during propagation (FIG. 7). Furthermore, the T7 acceptor phages have no fitness deficiency relative to wildtype when the tail fiber gene is provided from a donor plasmid (FIG. 7 and data not shown). Thus, the tail fiber gene is decoupled from the rest of the phage genome for interrogation of function. Next, phage variants are generated within the host during the infection cycle by Optimized Recombination by inserting tail fiber variants from a donor plasmid into the landing sites in the acceptor phage. To minimize biasing of variants during propagation, a helper plasmid constitutively provides the wildtype tail fiber in trans such that all progeny phages amplify comparably regardless of the fitness of any variant. At this stage, we typically have approximately 1 recombined phage among 1000 acceptor phages (FIG. 8). To enrich recombined phages in this pool, we passage all progeny phages on *E. coli* expressing Cas9 and a gRNA targeting the fixed sequence flanked by recombinase sites we introduced into the acceptor phage. As a result, only unrecombined phages will be inhibited while recombined phages with tail fiber variants are Accumulated. Recombined phages were highly enriched by over 1000-fold in the phage population when an optimized gRNA (data not shown) targeting the fixed sequence was used, whereas a randomized control gRNA yielded no enrichment of recombined phages (FIG. 9 and data not shown). In the final step, phages which were thus far propagated on hosts complementing wildtype tail fiber on a helper plasmid, are propagated on *E. coli* lacking the helper plasmid to under Library Expression of the variant tail fiber on the recombined phage. The distribution of a library tail fiber variants integrated on the phage genome after ORACLE was mildly skewed towards more abundant members but remained generally evenly distributed and comparable to the distribution of variants in the input donor plasmid library and retained 99.9% coverage (FIG. 10). Comparison of variant libraries with and without DNAse treatment was well correlated (R=0.994), indicating no unencapsidated phage genomes were influencing library distribution (data not shown). In summary, ORACLE is a generalizable tool for creating large, unbiased variant libraries of obligate lytic phages. These phage variants include variants that have a fitness deficiency on the host used to create the library and can all be characterized in a single selection experiment by deep sequencing phage populations before and after selection in a host. Compared to traditional plaque assays this represents increased throughput by nearly 3-4 orders of magnitude.

Example 2: DMS Screen of Tip Domain Variants in Different Bacterial Hosts

Deep mutational scanning (DMS) is a high-throughput experimental technique to characterize sequence-function relationships through large-scale mutagenesis coupled to selection and deep sequencing. The scale and depth of DMS could reveal sites for activity, specificity and stability in a protein. DMS has been employed to study enzymes, transcription factors, signaling domains, glycoproteins and various other proteins. To the best of our knowledge, no phage gene has been studied by DMS.

Bacteriophage T7 is a podovirus with a short non-contractile tail made up of three proteins including the tail fiber encoded by gp17. Each of the six tail fibers is a homotrimer composed of a relatively rigid shaft ending with a β-sandwich tip domain connected by a short loop. The tip domain is likely the very first region of the tail fiber to interact with host lipopolysaccharide (LPS) and position the phage for successful irreversible binding with the host. The tip domain is a major determinant of host specificity and activity and is often exchanged between phages to readily adapt to new hosts. Even single amino acid substitutions to this domain are sufficient to alter host range between *E. coli* strains. Due to its critical functional role, we chose the tip domain to comprehensively characterize activity and specificity by DMS.

Figure 11:
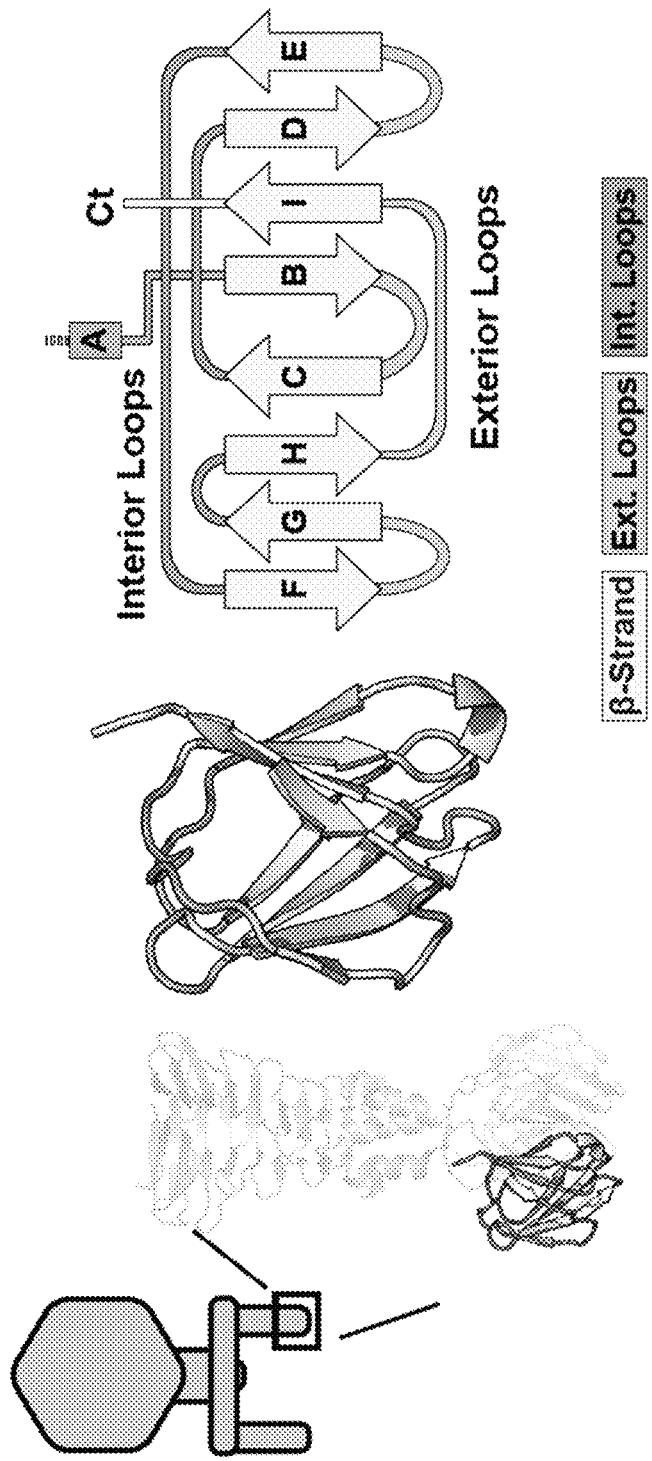
FIG. 11 shows a crystal structure and secondary structure topology of the tip domain color coded as interior loops, β-sheets and exterior loops.
Figure 12:
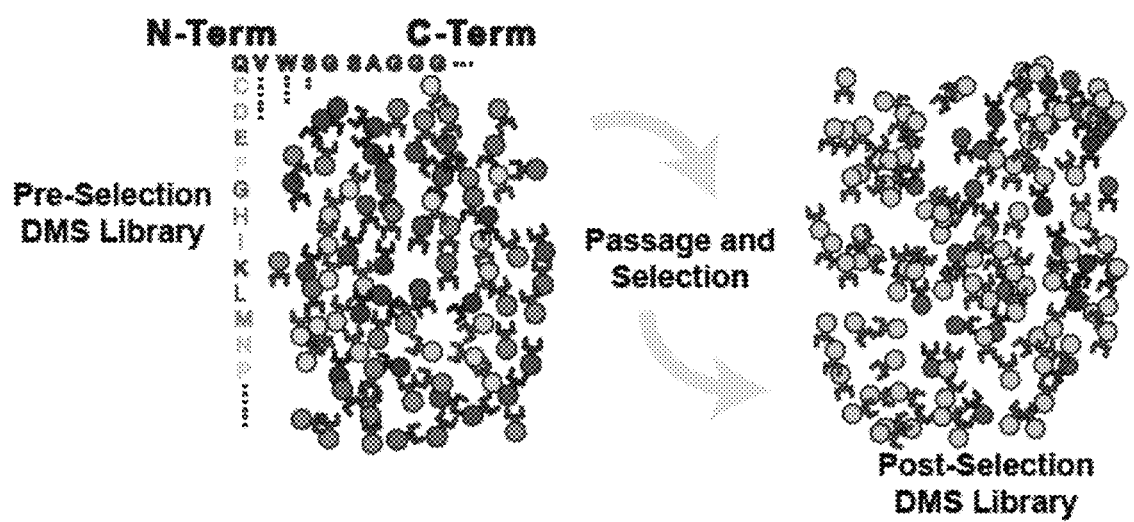
FIG. 12 shows a functional analysis of variants by comparing their abundances pre- and post-selection on a host.
Figures 13, 14, 15:
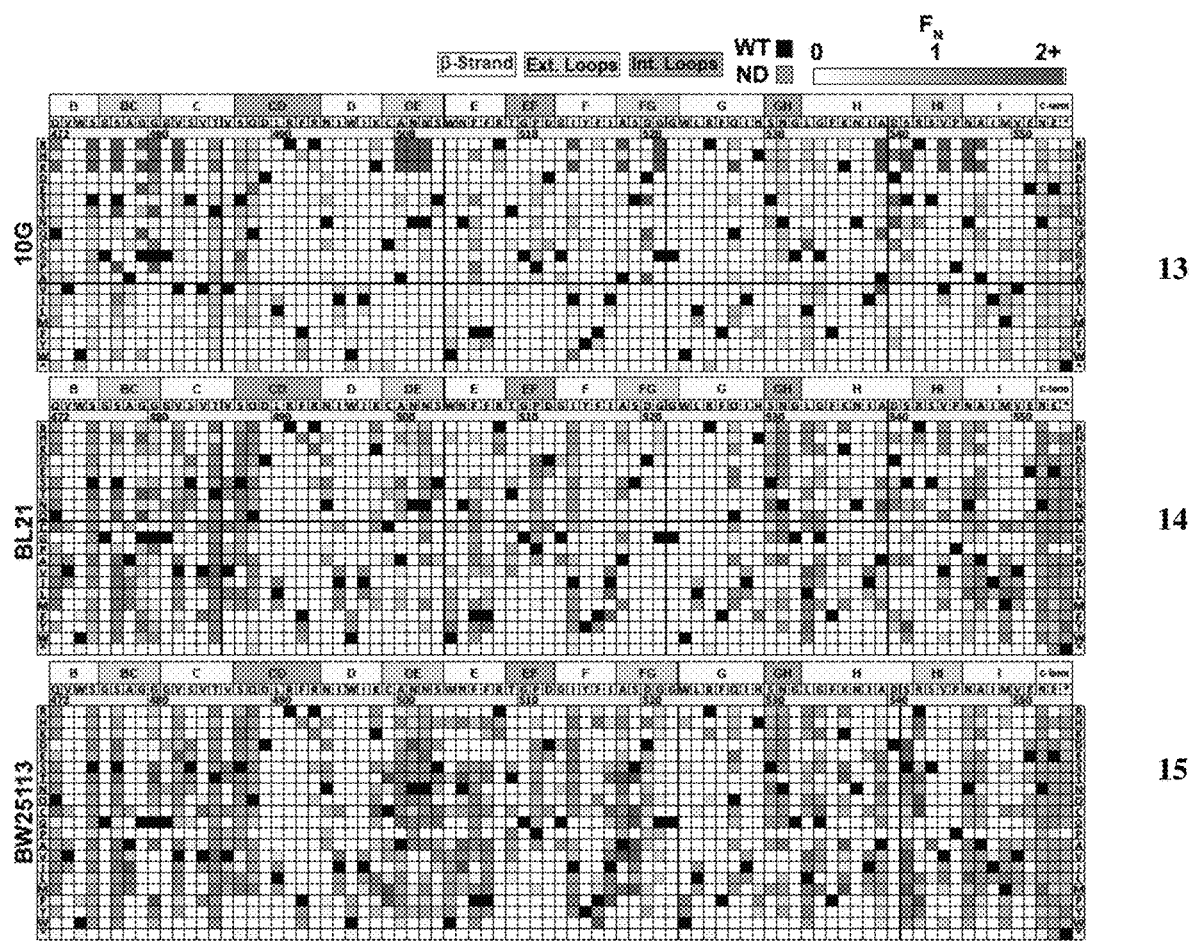
FIGS. 13-15 are heat maps showing normalized functional scores ($F_N$) of all substitutions (gray gradient) and wildtype amino acid (solid black) at every position for E. coli 10G (13), BL21 (14) and BW25113 (15). Residue numbering (based on PDB 4A0T), wildtype amino acid and secondary structure topology are shown above left to right, substitutions listed top to bottom.

We generated a library of 1660 single mutation variants of the tip domain, prespecified as chip-based oligonucleotides, where all nineteen non-synonymous and one nonsense substitution was made at each codon spanning residues 472-553 (FIG. 11), residue numbering based on PDB 4A0T. Using ORACLE, the library was inserted into T7 to generate variants to be selected and deep sequenced on three laboratory *E. coli* hosts: B strain derivative BL21, K-12 derivative BW25113 and DH10B derivative 10G. Each variant is given a functional score F based on the ratio of their relative abundance before and after selection, which is then normalized to wildtype to yield $F_N$ (FIG. 12-15, see methods). Selection on each host gave excellent correlation across biological triplicates (data not shown). To validate functional relevance of the screen, we hypothesized that the flexible C-terminal end (residues 551-553 and a three-residue extension with a substituted stop codon) is unlikely to have any structural or host recognition role. As expected, these positions broadly tolerated nearly all substitutions across all three strains indicating that the functional scores likely reflect true biological effects.

Figure 16:
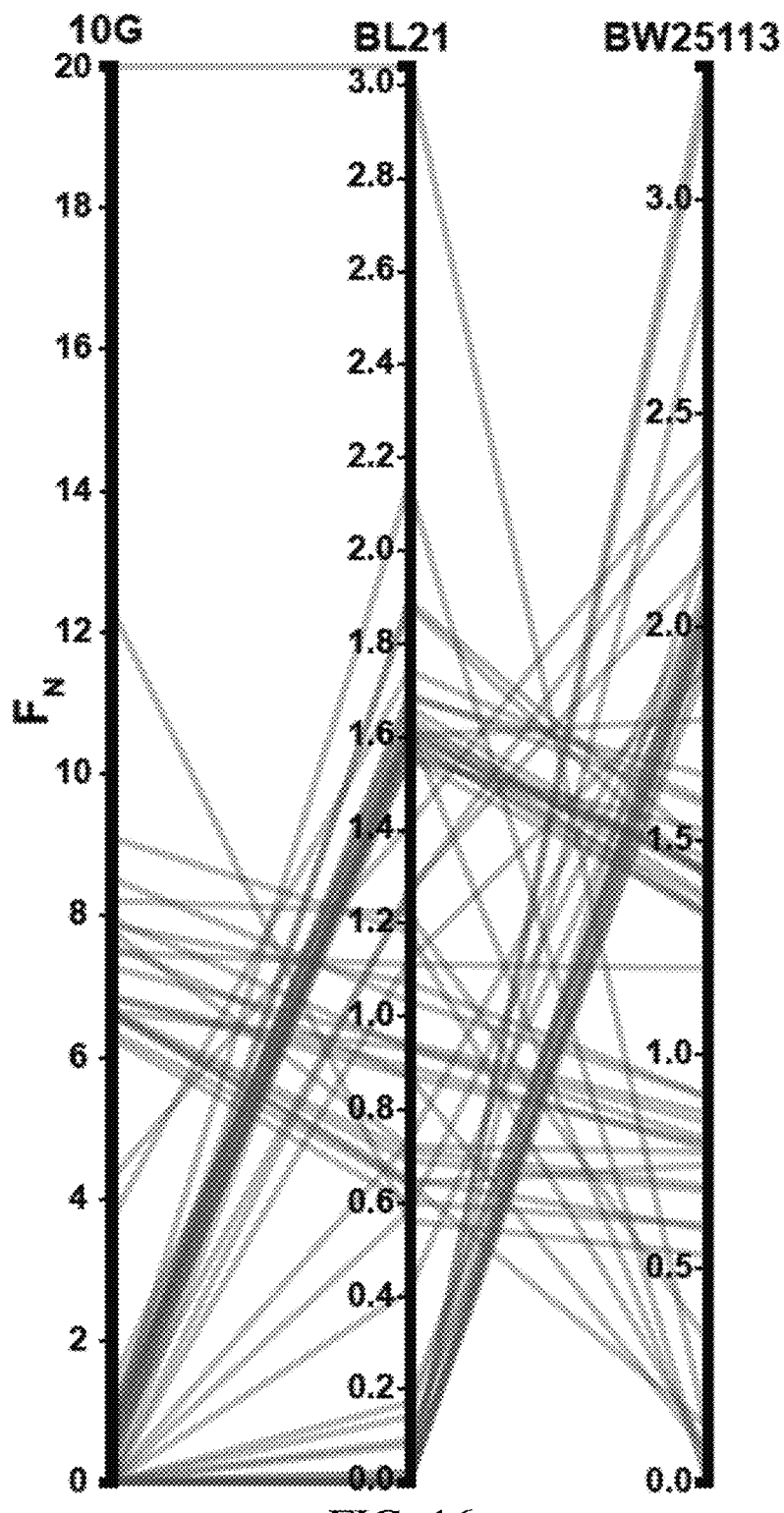
FIG. 16 shows a parallel plot showing $F_N$ for top 20 variants on 10G, BL21, and BW25113. Connecting lines indicate the ranking of a variant on other hosts. Variants with no connecting lines are depleted on other hosts.

We compared the activities of phage variants across hosts to assess their fitness and evolutionary adaptation to each host. Between the three hosts, T7 variants were most and least adapted to BW25113 and 10G, respectively, as evidenced by the fraction of depleted variants ($F_N<0.1$) after selection on each host (10G:0.66, BL21:0.59 and BW25113: 0.51). Further, wildtype T7 fared relatively poorly on 10G (F=0.77) indicating a fitness impediment but performed well on BL21 (F=2.92) and BW25113 (F=2.26). The fitness impediment gave many more variants competitive advantage ($F_N>2$) over wildtype on 10G (48 variants) compared to BL21 (2 variants) and BW25113 (16 variants) (data not shown). In fact, the best performing variants on 10G were 10 times more enriched than wildtype suggesting substantially higher activity (data not shown). Ranking of variants on each host (based on F score) gave us compelling evidence of the tradeoff between activity and host range (FIG. 16). The top ranked variants on each host were remarkably distinct from those on other hosts (except G479Q shared between 10G and BL21). Variants scoring highly on one host scored poorly on others (FIG. 16), but variants with intermediate scores performed well on all hosts. In effect, specialization toward a host comes at the cost of sacrificing breadth.

We investigated the physicochemical properties and topological preferences of substitutions after selection on each host. On 10G, there was pronounced enrichment of larger and more hydrophilic amino acids and depletion of hydrophobic amino acids (all p<0.001 FIG. S4D) which is visually striking on the heatmap (see R, K and H on FIG. 13). In contrast, no strong enrichment or depletion was observed on BL21 (data not shown). This is consistent with our earlier observation that wildtype T7 is generally well adapted to BL21 with the fewest outperforming variants. Since BL21 has been historically used to propagate T7, it is possible that T7 may have already adapted well to this strain over time. On BW25113, hydrophobic residues were modestly enriched (p<0.036), a trend opposite to 10G. This provides a molecular explanation for why high scoring substitutions on one host fare poorly on others. We mapped positions of enriched substitutions ($F_N>2$) onto the structure to determine topological preferences (data not shown). These fall predominantly on four exterior loops (BC, DE, FG and HI), regions of the adjoining region (β-strand H) close to exterior loop HI, and less frequently on the 'side' of the tip domain. This suggests directionality to phage-bacterial interactions and orientational bias of the tip domain with respect to bacterial surface.

Several key lessons emerged from the screens. First, single amino acid substitutions alone can generate broad functional diversity highlighting the evolutionary adaptability of the RBP. Second, T7 is not optimized and activity can be increased, even on hosts which T7 is considered to already grow well on. Third, enrichment patterns on each host follow broad trends but have nuance at each position.

Example 3: Comparison Across Strains Reveals Regions of Functional Importance Next, we sought to elucidate features of each residue position unique to each host and common across all hosts. There were over 30 sites with contrasting substitution patterns between different hosts revealing fascinating features of receptor recognition for T7. Here we focus on five of these sites, N501, R542, G479, D540, and D520 which showed starkly contrasting patterns (FIG. 17). N501 and R542 are located in exterior loops oriented away from the phage toward the receptor. In fact, R542 forms a literal 'hook' to interact with the receptor (FIG. 19). On 10G and BL21, only positively charged residues (R, K and H) were tolerated at residues 501 and 542 while in contrast many more substitutions were tolerated at both residues on BW25113. One such substitution, R542Q is the best performing variant on BW25113 ($F_N=3.31$) but is conspicuously depleted on 10G and BL21 suggesting that even subtle molecular disparities can lead to large biases in activity. The substitution profiles of G479 and D540 are loosely the inverse of N501 and R542 as many substitutions are tolerated on BL21 and 10G, but very few are tolerated on BW25113. Since D540, a receptor-facing position on an exterior loop, is only 6 Å from G479, it is likely that any substitution at G479 may sterically hinder D540, resulting in similar substitution patterns (FIG. 17). This hypothesis is further supported by enrichment of adjacent S541D on BW25113 ($F_N=2.82$, the third highest scoring substitution) while this substitution is depleted on 10G and BL21. D520 displays the third variation in substitution patterns where substitutions are generally tolerated on 10G and BW25113, but not tolerated on BL21. Overall, these host-specific substitution patterns reveal nuanced relationship between tip domain composition and receptor preferences.

Next, we quantitatively characterized the role of every residue by integrating selection data across all strains to reveal a functional map of the tip domain at granular resolution (FIGS. 18 and 19). We classified every position as 'intolerant', 'tolerant' and 'functional' based on aggregated $F_N$ of all substitutions across all three strains at every position. Positions where the majority of substitutions were depleted were considered intolerant to substitution, while positions where at least a third of substitutions were depleted in one strain and tolerated or enriched in another strain were considered functional, the remaining positions were considered tolerant. The hydrophobic core comprising W474, I495, W496, I497, Y515, W523, L524, F526, I528, F535 and I548 which is essential for stability is highly intolerant to substitutions (FIG. 18). Other intolerant positions include an elaborate network of salt bridges involving D489, R491, R493, R508 and D512 in the interior loops, which likely constrain the orientation of the tip domain relative to the shaft (FIG. 19). Interestingly, glycines (G476, G510, G522 and G532) which normally tend to be mutable are highly intolerant to substitutions. These glycines may be essential to minimize steric obstruction to adjacent larger residues similar to G479 and D540 on BW25113 (FIG. 19). For example, G510 and G532 may facilitate formation of salt bridges in the interior loop, while G476 and G522 may facilitate a required interaction in exterior loops for all three hosts. Functional positions typically point outward and are densely concentrated along exterior loops BC, DE, FG and HI. This is consistent with specificity switching substitutions found in previous studies, D520Q and V544A, which are both located in exterior loops. Functional positions were also found in regions other than exterior loops albeit less frequently, such as I514, Q527 and K536 which are adjacent β-sheet residues, along one side of the tip domain (FIG. 19). This suggests the phage can use the 'side' of the tip domain to engage the receptor, increasing the apparent functional area of the tip domain.

We also determined if the functionally important regions could have been predicted computationally, as the ability to predict functionally important regions without DMS could rapidly accelerate engineering efforts. We used Rosetta, a state-of-the-art protein modeling software, to calculate the change in the change in Gibbs free energy (ΔΔG) individually for each of the 1660 mutations and compared this distribution to our DMS results (data not shown). In summary, predicted thermodynamic changes in stability mapped very well with over 93% of tolerated or functional positions predicted to have favorable ΔΔG energies. Incorporating stability estimations could further improve the engineering power of the assay, for example by predicted stable positions with intolerant $F_N$ may indicate residues necessary for all three strains.

Overall, these results paint a complex enrichment profile for each strain with some broad trends but subtle strain-specific effects. These results suggest that exterior loops and some outward facing positions in β-sheets act as a reservoir of function-switching and function-enhancing mutations, likely promoting host-specific and orientation-dependent interactions between phage and bacterial receptors. Functional positions identified by this comparison are ideal engineering targets to customize host range and activity.

Example 4: Discovery of Gain-of-Function Variants Against Resistant Hosts

Figure 20:
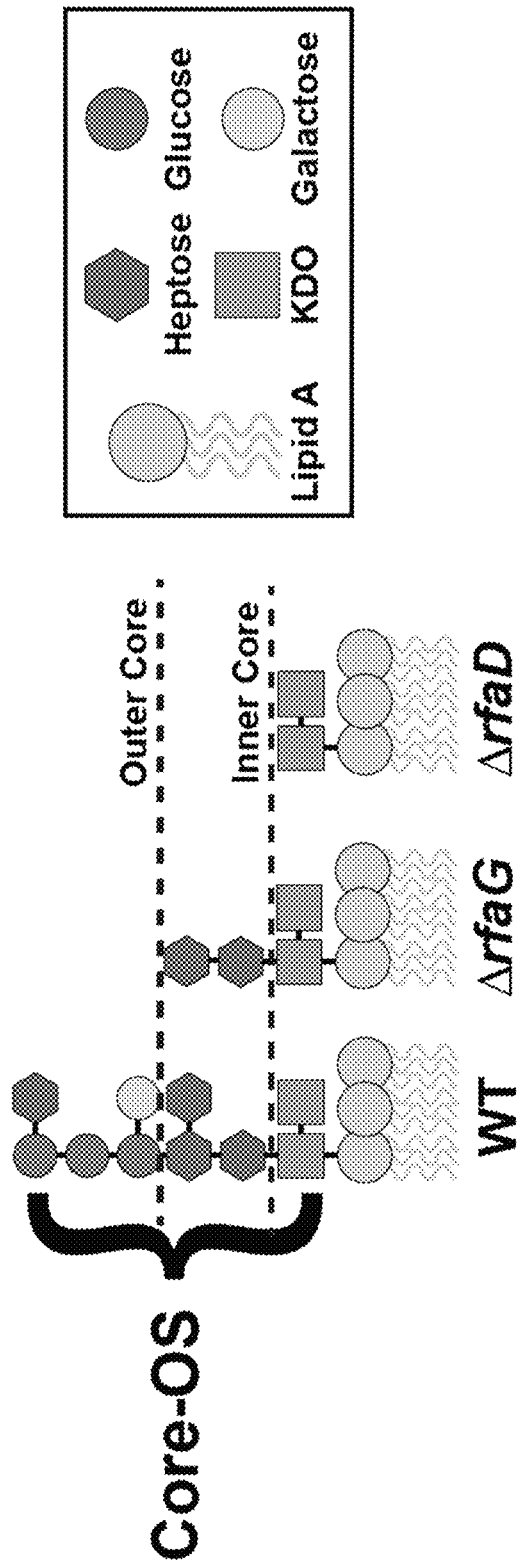
FIG. 20 shows a schematic view of the LPS on wildtype BW25113, BW25113ΔrfaG and BW25113ΔrfaD.
Figures 21, 22:
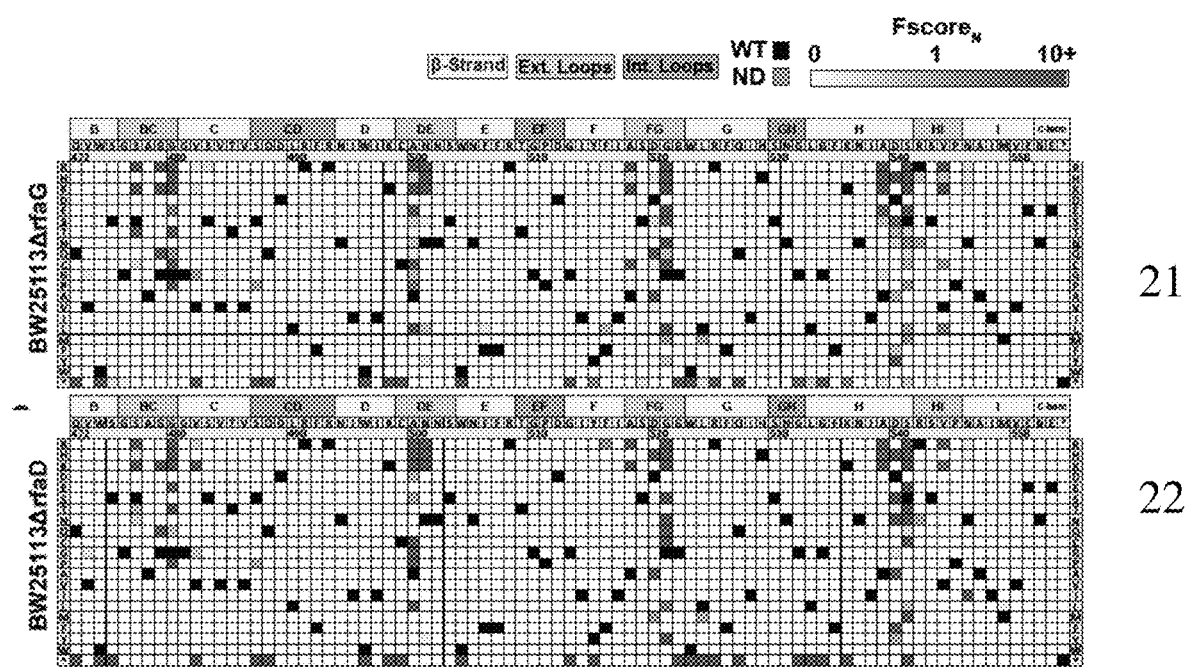
FIGS. 21 and 22 are heat maps showing normalized functional scores ($F_N$) of all substitutions (gray gradient) and wildtype amino acid (solid black) at every position for BW25113ΔrfaG (21) and BW25113ΔrfaD (22).
Figure 25:
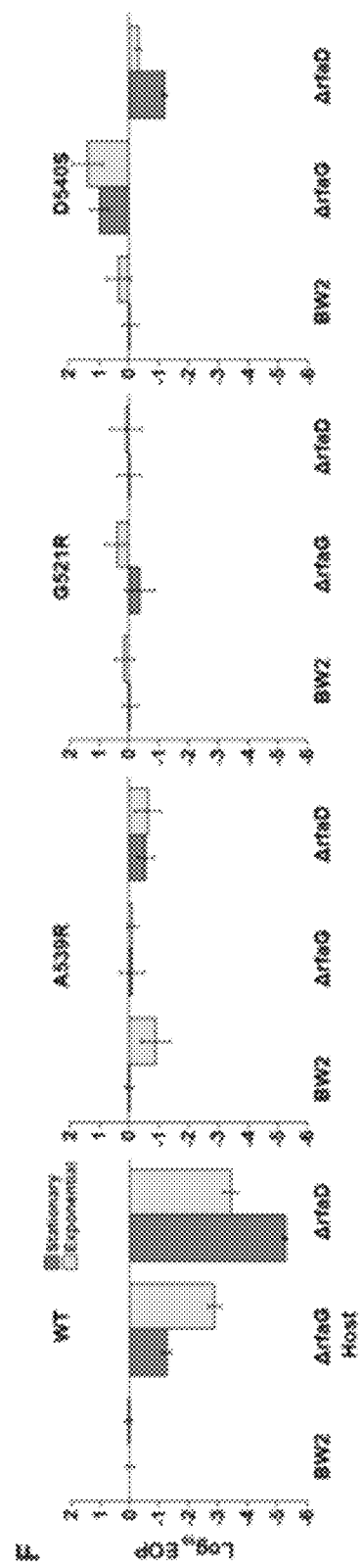
FIG. 25 shows EOP (mean±SD, biological triplicates) for wildtype and select variants on BW25113, BW25113ΔrfaG and BW25113ΔrfaD in exponential (dark gray) and stationary phases (light gray) using BW25113 as a reference host.

The tail fiber is considered a reservoir of gain-of-function variants due to its principal role in determining fitness of a phage through host adsorption. We hypothesized that novel gain of function variants against a resistant host could be discovered by subjecting our tail fiber variant library to selection on a resistant host. To identify a resistant host, we focused on genes rfaG and rfaD involved in the biosynthesis of surface lipopolysaccharide (LPS) which is a known receptor for T7 in *E. coli*. Gene rfaG (synonyms WaaG or pcsA) transfers glucose to the outer core of LPS and deletion mutants lack the outer core of LPS, while rfaD (synonyms gmhD or WaaD) encodes a critical epimerase required for building the inner core of LPS (FIG. 20). Deletion of either gene reduces the ability of T7 to infect *E. coli* by several orders of magnitude (FIG. 25). We challenged the library of T7 variants against *E. coli* deletion mutant strains BW25113ΔrfaG and BW25113ΔrfaD through pooled selection and sequencing as before (FIG. 11), and determined a $F_N$ score for each substitution on both strains (FIG. 21,22). Independent replicates showed good correlation for BW25113ΔrfaG (R=0.99, 0.93, 0.93) but only adequate correlation for BW25113ΔrfaD (R=0.51, 0.68, 0.39) (data not shown). Although the scale of $F_N$ was inconsistent across replicates on BW25113ΔrfaD, the same substitutions were largely enriched in all three replicates, suggesting reproducibility of results. Inconsistencies in $F_N$ scores may arise due severe loss of diversity causing stochastic differences in enrichment to become magnified across independent experiments.

Figure 23:
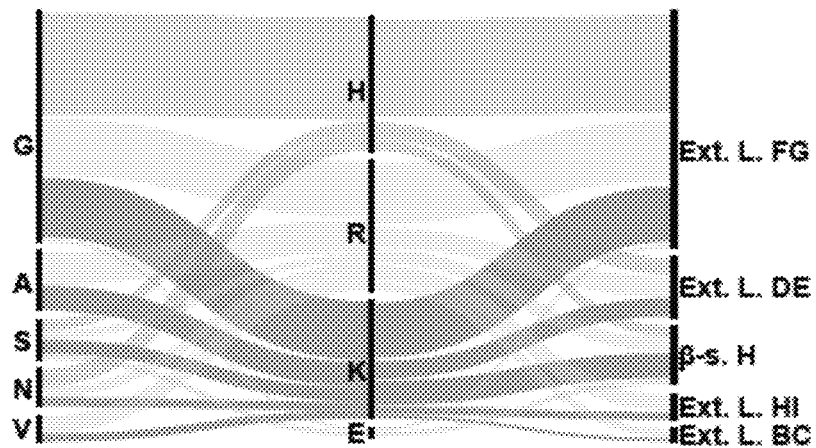
FIGS. 23 and 24 show among highly enriched variants ($F_N>10$), targeted amino acids (left), their substitutions (middle) and topological location on the structure (right) on BW25113ΔrfaG and BW25113ΔrfaD
Figure 24:
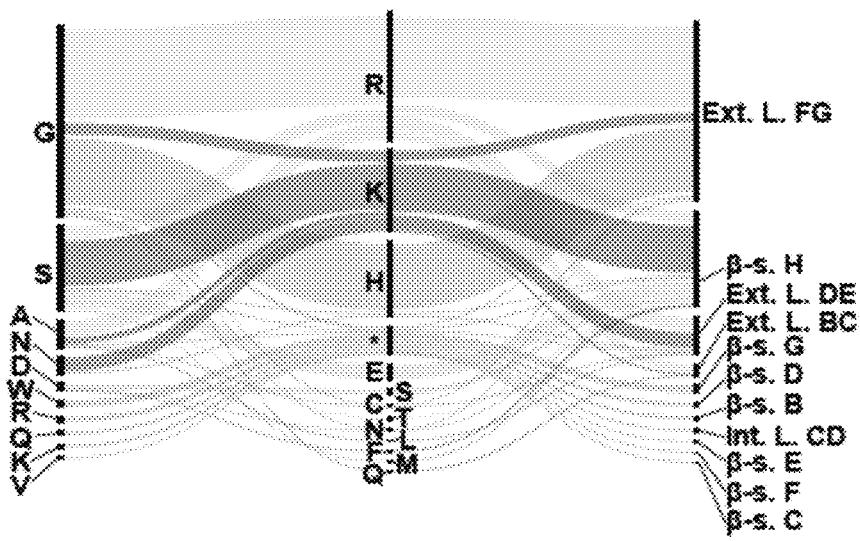

We found several gain-of-function T7 variants that could infect both deletion mutant strains with activity comparable to wildtype T7 infecting susceptible BW25113 (FIG. 25). Low sequence diversity and high enrichment scores of T7 variants indicates a strong selection bottleneck which is consistent with diminished activity of wildtype T7 on the deletion mutants. This is reflected in the low functional score of wildtype on both strains (BW25113ΔrfaG F=0.1, BW25113ΔrfaD F=0.03) which, for comparison, is significantly lower than wildtype BW25113 (F=2.26). The number of enriched variants outperforming wildtype T7 ($F_N$>2) on the deletion mutants (BW25113ΔrfaG: 68 variants, 4.1% and BW25113ΔrfaD: 55 variants, 3.3%) was much higher than BW25113 (16 variants, 1%) but comparable to 10G (48 variants, 2.9%) (data not shown). However, the enrichment scores of top performing variants such as G521H and G521R on BW25113ΔrfaG and S541K and N501H on BW25113ΔrfaD was over 100 times greater than wildtype T7, suggesting strong gain-of-function on the deletion mutant strains (data not shown). Of the 78 substitutions with $F_N$>2 on either deletion strain, 45 substitutions had $F_N$>2 on both strains indicating that variants that performed well on one strain typically performed well on the other strain. This implies the enriched substitutions may have broad affinity for truncated LPS but cannot discriminate based on the length of the LPS. Nonetheless, hydrophilic substitutions were more strongly enriched on BW25113ΔrfaG (p<0.0011), but not on BW25113ΔrfaD (p<0.29) suggesting subtle differences in surface chemical properties of deletion strains leading to host-specific enrichments (data not shown). Indeed, there were several variants with contrasting F scores on both strains such as S541T (BW25113ΔrfaD $F_N$=44.8, BW25113ΔrfaG $F_N$=0.6) and G521E (BW25113ΔrfaD $F_N$=0, BW25113ΔrfaG $F_N$=17.4) suggest potential host preference. The vast majority of mutations were concentrated in the exterior loops BG, FG, HI and β-strand H, all pointing downwards towards the bacterial surface, reinforcing the functional importance of these regions of the tip domain (FIGS. 23 and 24). Notably, the most enriched variants had large positively charged substitutions (K, R and H) akin to the enrichment pattern on 10G, suggesting bacterial surface of these truncated mutants likely resembles that of 10G. Our results are consistent with a recent continuous evolution study, which identified G480E and G521R as possible gain-of-function variants on a strain similar to BW25113ΔrfaD and G479R and G521S as possible gain of function variants on BW25113ΔrfaG, although these variants only represent a small fraction of the gain of function discovered in our study.

We validated the results of the pooled selection experiment by clonally testing the ability of phage variants with high $F_N$ (A539R, G521H, and D540S) to plaque on the deletion strains based on a standard efficiency of plating assay (EOP). Indeed, EOP results showed significant gain of function in these variants on the deletion strains (FIG. 25). D540S was particularly noteworthy as it performed better on the deletion strain BW25113ΔrfaG over wildtype BW25113 by 1-2 orders of magnitude. Based on these results, we conclude that D540 is critical for infecting wildtype BW25113 (FIG. 17-19) because Asp at this position likely interacts with the outer core of LPS. As a consequence, when the outer core of the LPS is missing (BW25113ΔrfaG), a substitution at this position becomes necessary for adsorption either to a different LPS moiety or to an alternative receptor.

We introduced stop codon at every position to systematically evaluate the function tip domains truncated to different lengths. Many truncated variants performed well, especially on BW25113ΔrfaG which included some with $F_N$>10. We clonally tested variant R525*, the best performing truncated library member (BW25113ΔrfaG $F_N$=9.55, BW25113ΔrfaD $F_N$=75.7), and found that this mutant showed no ability to plaque on any host unless provided gp17 in trans. These truncated phages, detectable here only using NGS, may demonstrate how obligate lytic phages could become quiescent in a bacterial population, slowly replicating alongside their bacterial hosts, requiring only a single mutation to become active again. In fact, acceptor phages altogether lacking a tail fiber were present at extremely low abundance. These phages are not artifacts from library creation as some ability to replicate would be required to produce detectable concentrations of each phage. We concluded that these are viable phage variants albeit with a much slower infection cycle resulting in their inability to form visible plaques.

Example 5: Selection of Active T7 Variants to Kill Pathogenic *E. coli* Causing Urinary Tract Infection (UTI)

Phage therapy is emerging as a promising solution to antibiotic resistance crisis. Recent success stories in the clinic against multidrug resistant *Acinetobacter* and *Mycobacterium* showcase the enormous potential of phage therapy. However, these stories also highlight fundamental challenges in developing phage-based therapeutics. Bacteria often quickly recover after phage application, indicating low phage susceptibility and rapid emergence of bacterial resistance. Although initial application of phages reduces bacterial levels, the residual bacterial load remains high, resulting in their recovery. Even this limited activity is achieved with only extremely high dosage, a lab equivalent of high phage to bacteria ratios (multiplicity of infection or MOI), that may not be feasible or desirable in clinical applications. We hypothesized that tip domain variants may be able to abate bacterial resistance and be active even at low phage dosage by better adsorbing to the native receptor or recognizing a new bacterial receptor altogether.

Figure 26:
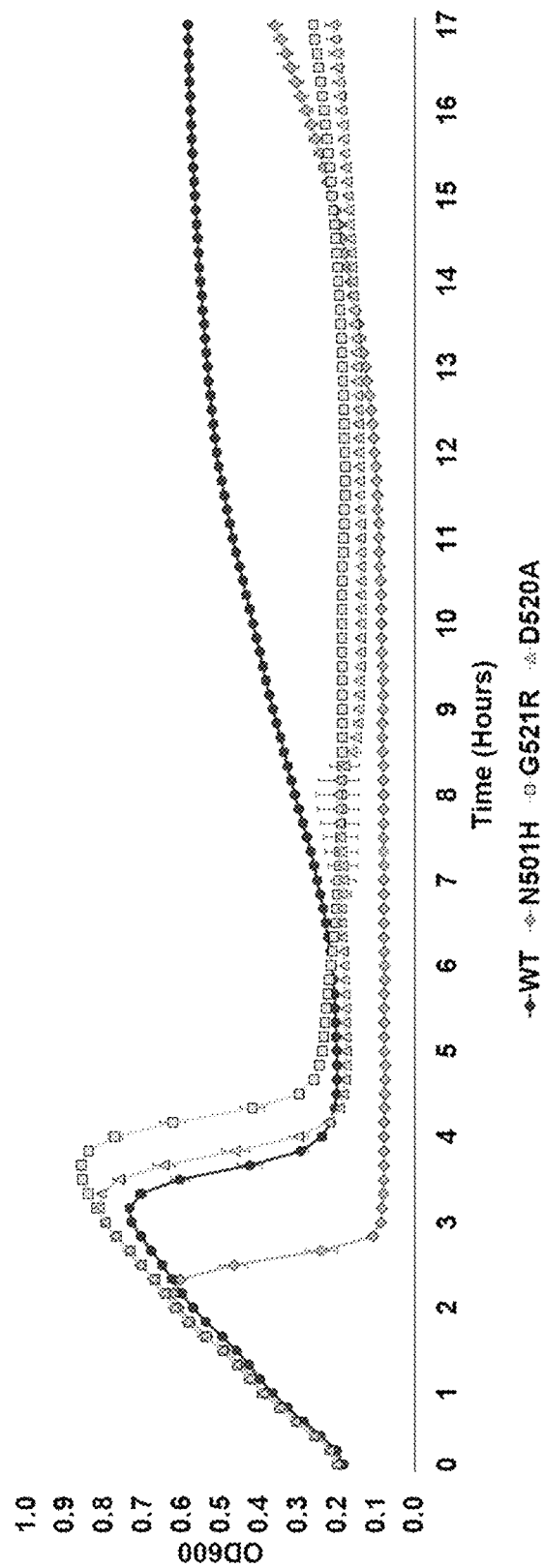
FIG. 26 shows a growth time course of UTI strain subject to wildtype T7 and select variants. Phages were applied after an hour at an MOI of approximately $10^{-2}$
Figure 27:
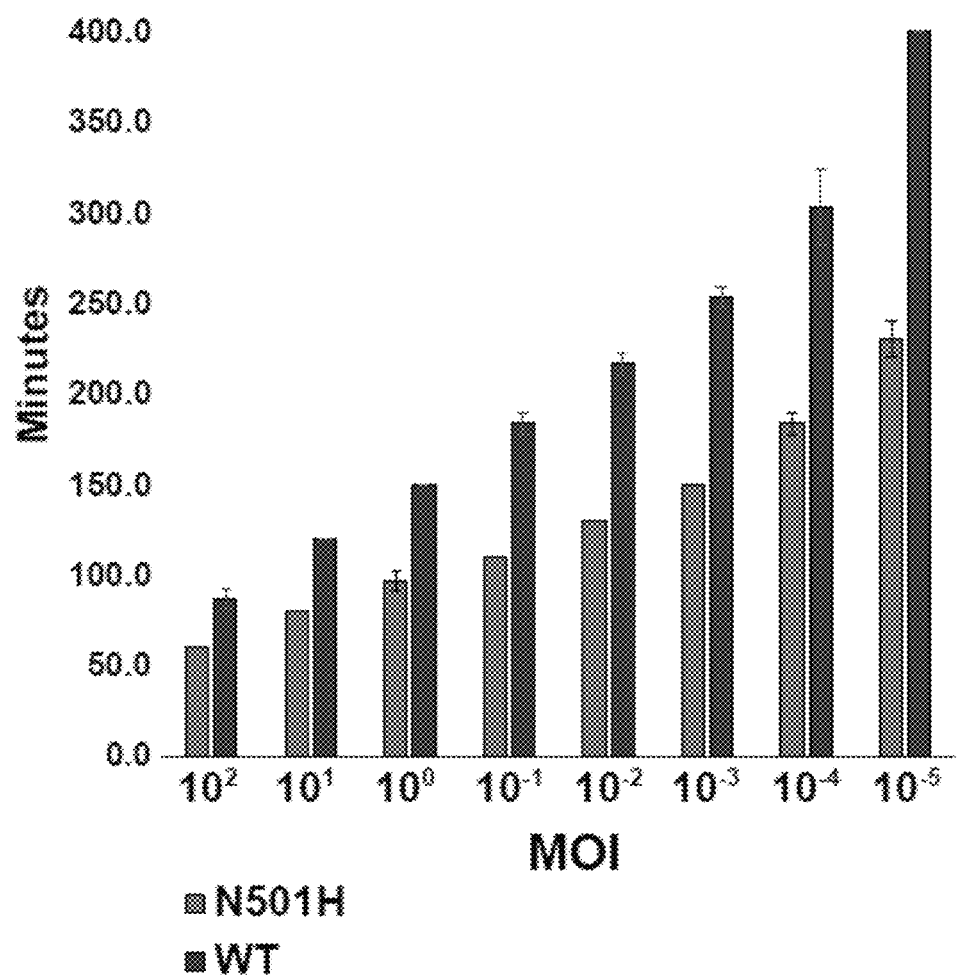
FIG. 27 shows estimated time to lysis of UTI strain incubated with wildtype T7 and N501H variant over a range of MOIs, derived from time course experiments.

To test this hypothesis, we chose a pathogenic *E. coli* strain from the Goldstein collection isolated from a patient with urinary tract infection (UTI). Although T7 can infect the UTI strain, resistance arises rapidly, a phenomenon all too common with the use of natural phages. EOP assays for wildtype T7 showed resistant plaque morphology in stationary and exponential cultures indicative of rapidly emerging resistance (data not shown). No visible lysis was detected when wildtype T7 was applied in liquid culture (MOI=1). However, the variant library applied on the UTI strain cleared the culture (MOI=1) suggesting T7 variants capable of lysing and attenuating resistance exist in the pool. We clonally characterized three variants (N501H, D520A and G521R) isolated from plaques. All three variants vastly outperformed wildtype T7 in terms of onset of resistance. Resistance emerged approximately 11-13 hours after initial lysis for the three variants whereas it took merely 1-2 hours for wildtype (FIG. 26). In particular, N501H variant lysed cells faster and produced lower bacterial load post lysis suggesting far greater activity compared to wildtype T7. Next, we compared the effect of phage dosage (MOI=$10^2$-$10^5$) on lysing activity of N501H variant and wildtype T7 (FIG. 27). At lower MOI, time to lysis of N501H variant was half of wildtype T7, though they were comparable at higher MOI.

Figure 28:
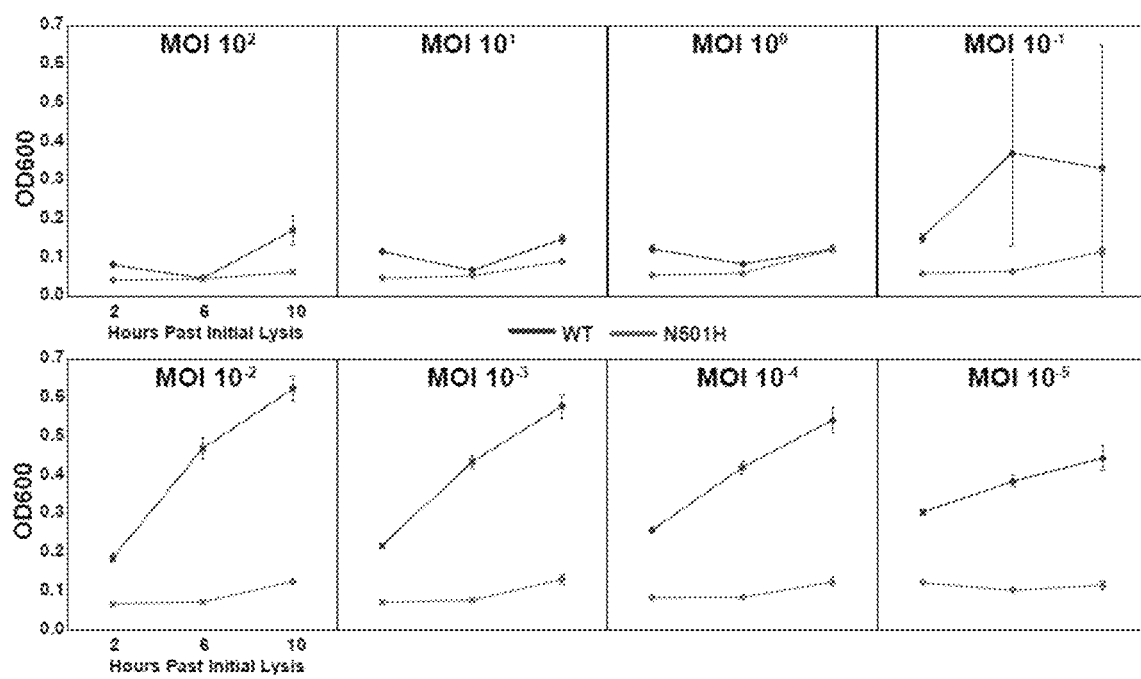
FIG. 28 shows cell density (OD600) of UTI strain when incubated with wildtype T7 and N501H variant at select timepoints after initial lysis. All data represented as mean±SD of biological triplicate.

A striking contrast between N501H variant and wildtype T7 is evident in the suppression of resistance at progressively lower MOI (FIG. 28). Between MOI of 100 to 1, both N501H variant and wildtype perform similarly. However, between MOI of $10^{-1}$ and $10^{-5}$, N501H variant suppresses resistance over a 10-hour window, while wildtype phages are quickly overcome by the bacterial resistance. Without being held to theory, we postulate that at high MOI wildtype T7 simply overwhelms the host before resistance arises due to multiple infection events happening simultaneously, a known outcome for high MOI condition. At lower MOI, resistance can emerge, and only phages adapted to the host can effectively kill the host. Interaction at high phage to bacteria ratios is not guaranteed in a clinical setting and activity cannot be dosage-dependent, and these results indicate that passage with phages with this substitution enabled more active phages to develop that were capable of overcoming resistance in UT1473.

Example 6: Global Comparison of Host Preferences Across Variants

Most phage species are "specialists" that selectively target a narrow range of bacterial hosts but avoid other closely related hosts. We wanted to assess differences in the host range of individual variants on 10G, BL21 and BW25113 and identify variants with constricted host ranges. Ideally, host specificities can be determined by subjecting a co-culture of all three hosts to the phage library. However, deconvolving specificities of thousands of variants from a pooled co-culture experiment can be technically challenging. Instead, we sought to estimate specificities by comparing $F_N$ of a phage variant on all three strains. Although $F_N$ compares activity of variants within a host, it could nonetheless be a useful proxy for estimating specificities across strains. For instance, a phage variant with high $F_N$ on BL21 but completely depleted on BW25113 is likely to specifically lyse BL21 than BW25113 in a co-culture experiment. Based on this rationale, we considered different metrics of comparison of $F_N$, and settled on difference in $F_N$ of a variant with less weight for enrichment (or $F_D$, see methods) between any two hosts as an approximate measure of host preference. This metric is not an absolute measure of strain specificity, but one devised to reveal broad trends in specificity to prioritize variants for downstream validation.

Figure 29:
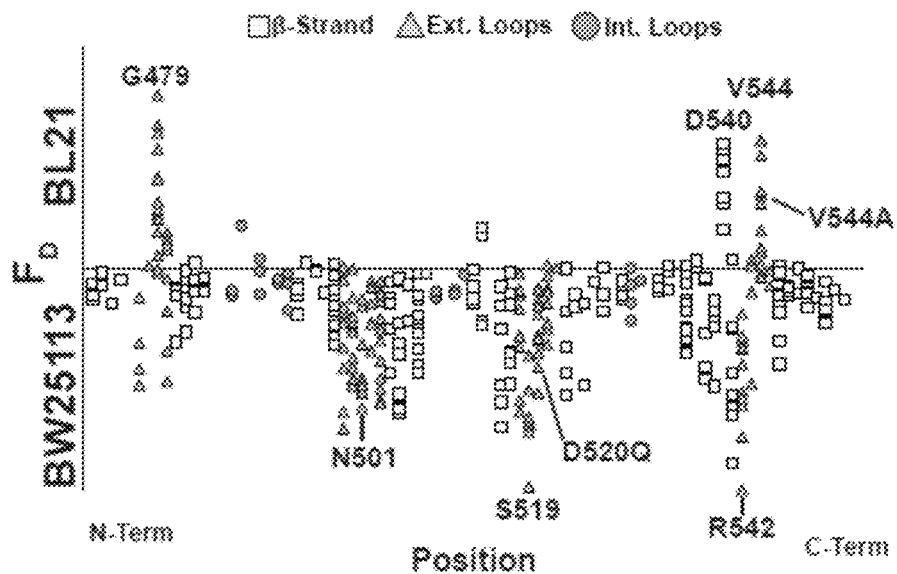
FIGS. 29-31 show pairwise comparison of differences in functional scores of variants between hosts (see Methods). Variants above the line favor lysis of strain noted above the line, and vice versa for variants below the line.
Figure 30:
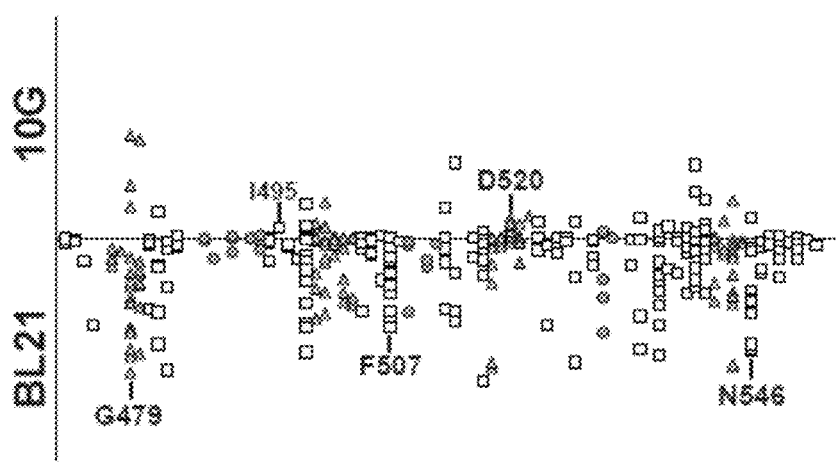
Figure 31:
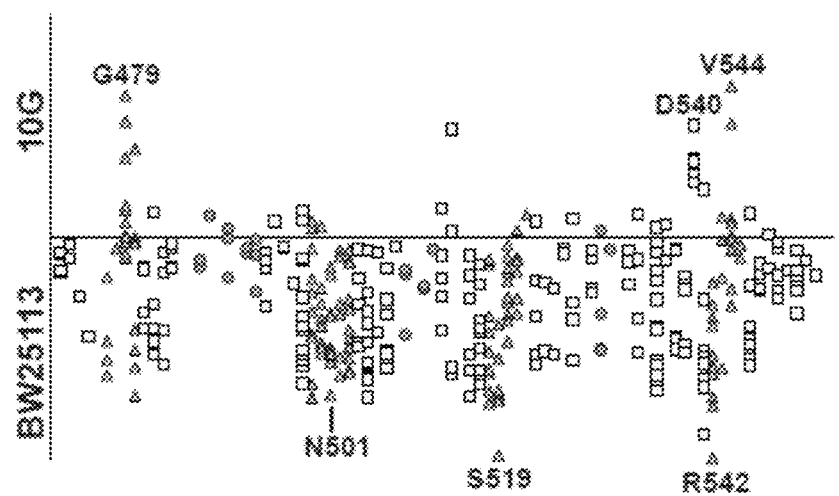

To assess if variants preferred one strain over another, we computed $F_D$ for all three pairwise combinations and plotted functional substitutions as points on or above/below a 'neutral' line (FIG. 29-31). Variants above the line favor lysis of strain noted above the line, and vice versa for variants below the line. To check if this $F_D$-based approach is suitable for assessing strain specificity, we compared our results with previously published data. Two substitutions, D520Q and V544A, that were reported to have a preference for BW25113 and BL21, respectively, in head to head comparisons would be placed correctly in our plots, confirming the validity of our $F_D$-based classification scheme. We identified 118 variants (($|F_D|>=1$ out of 1660 variants) with possible constricted host range. Of the 118 variants, 53 variants favor BW25113 over BL21 and 98 variants favor BW25113 over 10G in pairwise comparisons (FIGS. 29 and 31). Between BL21 and 10G, there are 15 ideal variants ($|F_D|>=1$) that favor BL21 but none that favor 10G (FIG. 30). A strong preference for BW25113 among a majority of variants is clearer in a ternary plot where points closer to a vertex indicate greater preference for the strain at the vertex (data not shown).

Certain key positions including G479, D540, R542 and D520 which we identified as functionally important (FIG. 17) are the molecular drivers of specificity between hosts (FIG. 29-31). Taken together, our data suggests that it would be easier to find a variant capable of specifically lysing BW25113, less so for BL21, and most challenging for 10G.

Figure 32:
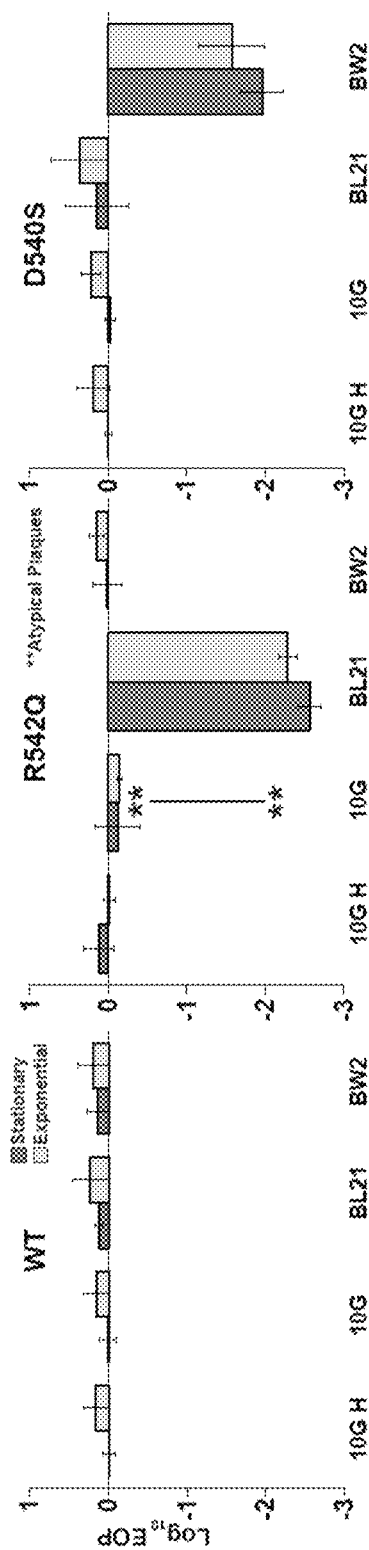
FIG. 32 shows EOP (mean±SD, biological triplicates) for wildtype T7 and select variants on BW25113, 10G and BL21 in exponential (dark gray) and stationary phases (light gray) using exponential 10G with gp17 on helper plasmid (10G H) as a reference host. R542Q plaques are atypically small until EOP approximately $10^{-2}$.

To validate our analysis, we chose phage variants R542Q which had a greater preference for BW25113 than BL21 or 10G (BW25113 $F_N$=3.31, BL21 $F_N$=0, 10G $F_N$=0) and D540S which had a greater preference or BL21 and 10G than BW25113 (10G $F_N$=1.56, BL21 $F_N$=0.62, BW25113 $F_N$=0.03) for clonal testing. Indeed, R542Q showed ~100-fold decrease in ability to plaque on BL21 than on BW25113 while 10G plaques were atypically small, indicating a severe growth defect (FIG. 32, data not shown). In contrast, D540S showed ~100-fold decrease in ability to plaque on BW25113 than on BL21 and 10G (FIG. 32) confirming host constriction properties of chosen variants. In summary pairwise comparison is a powerful tool to map substitutions that constrict host range that can be leveraged to tailor engineered phages for specific target hosts.

DISCUSSION

In this study, we used ORACLE to create a large, unbiased libraries of T7 phage variants to comprehensively characterize the mutational landscape of the tip domain of the tail fiber. Our study identified hundreds of new function-enhancing substitutions than have not been previously identified. We mapped regions of function-enhancing substitutions on to the crystal structure to elucidate how sequence and structure influence activity and host range. Several key insights emerged from these results. Cross-comparison between different hosts and selection on resistant hosts allowed us to map key substitutions leading to host discrimination and gain of function. Single amino acid substitutions are sufficient to enhance activity and host range including some that confer dramatic increases in activity or specificity. The functional landscape on each host was unique, reflecting both different molecular preferences of adsorption and the fitness of wildtype on these strains. For instance, hydrophilic substitutions were enriched in TOG while hydrophobic substitutions were enriched in BW25113. Notably, substitutions on TOG (an E. coli K-12 derivative lacking LPS components) mirrored substitutions that recovered function on BW25113 mutants with truncated LPS which shows convergence of selection. Function-enhancing substitutions were densely concentrated in the exterior loops indicating an orientational preference. However, they were also found on other surface residues, albeit less frequently, suggesting alternative binding modes of the tip domain for host recognition. Taken together, these results highlight the extraordinary functional potential of the tip domain and rationalizes the pervasive use of the β-sandwich fold in nature for molecular recognition.

These results also highlight the power of deep sequencing to detect and resolve small functional effects over traditional low-throughput plaque assays. This is best illustrated in the case of truncated variants visible only to deep sequencing, but incapable of plaque formation without a helper plasmid. The truncated variants are likely not experimental artifacts as some ability to replicate would be required to survive multiple passages on the host. Truncation of the tip domain may misorient the phage relative to the receptor likely resulting in slower growth and deficiency in plaquing. Since plaque formation is a complex process, inability to plaque may not imply a functionally-incompetent phage.

ORACLE could emerge as a foundational technology to elucidate sequence-function relationships due to its generalizability to any phage gene and applicability other phages. On T7, ORACLE can be used to investigate the function of several important genes including the remainder of the tail fiber and tail structure, capsid components, or lysins and holins. Together, these will provide a comprehensive view of molecular determinants of structure, function and evolution of a phage. Once the phage variants are created, scaling up ORACLE to investigate potentially tens of hosts will merely scale up sequencing volume, not experimental complexity. Such a large-scale study will lead to a detailed molecular understanding and adaptability of phage bacterial interactions. Any phage with a sequenced genome and a known propagation host should be amenable to ORACLE because the phage variants are created during the natural infection cycle. This approach can be leveraged to tune activity for known phages with high activity, such as T7, or to identify engineering targets to dramatically increase activity for newly isolated natural phages.

The confluence of genome engineering, high-throughput DNA synthesis and sequencing enabled by ORACLE together with viral metagenomics could revolutionize phage biology. Phages constitute unparalleled biological variation found in nature and are aptly called the "dark matter" of biosphere. Their sequence diversity and richness are coming to light in the growing volume of viral metagenome databases. However, what functions these sequences encode remains largely unknown. For instance, fecal viromes estimate $10^8$-$10^9$ virus-like particles per gram of feces, but less than a quarter of sequence reads align to existing databases. While this knowledge gap is daunting, it also presents an opportunity to mine the enormous functional potential metagenomic sequences to characterize their function and engineer programmable phages. By enabling sequence programmability, we envision ORACLE as a powerful tool to discover new phage 'parts' from metagenomic sequences.

We advance anew framework for effective, reliable and rapid development of potent therapeutic phages by high-throughput precision engineering of natural chassis phages to create phage variants with desired properties. The use of natural phages for phage therapy has fundamental limitations in activity, reliability, scalability and speed. Natural phages have lower activity due evolutionary constraints, give inconsistent results in unwieldy cocktails, and discovery new phages when bacterial resistance arises is slow and laborious. The sequence-functional knowledgebase created from ORACLE experiments will facilitate a design-build-test-learn platform guided by machine learning for engineering new phages against new and resistant bacterial strains.

The several examples described above illustrate how the ORACLE method described herein may be used to generate large, unbiased libraries of phage variants to comprehensively characterize the mutational landscape of a protein of interest, such as phage T7 RBP tail fiber tip domain, in this instance.

Example 6: Generalizability of Oracle to Phage Libraries with Multiple Substitutions ORACLE can be used to create libraries of T7 bacteriophage with many different substitutions. ORACLE has been used to make a phage library of double and triple substitutions, and another phage library consisting of members with one to ten substitutions. Additionally, a library of T7 bacteriophage was made using ORACLE where the C-terminal 83 amino acid region of the tail fiber was exchanged for carbohydrate binding domains ranging from 11 to 60 amino acids. These libraries were all made by altering the gene on the plasmid library used for recombination during ORACLE, the overall method for ORACLE does not change. Table 1 shows the percentage of library members integrated into the phage from the plasmid library during ORACLE for each of these libraries. These libraries were integrated and expressed at similar efficiencies to the library of single substitutions.

TABLE 1

Summary of ORACLEs Ability to Integrate and Express Various T7 Phage Libraries

| Library Description | Plasmid Library Size | Library Members integrated into phage after ORACLE | Percentage Integrated |
|---|---|---|---|
| Single substitutions | 1660 | 1657 | 99.8% |
| Double and triple substitutions | 9639 | 9259 | 96.1% |
| From one to ten substitutions | 13084 | 12336 | 94.3% |
| C-terminal region exchanged | 3555 | 3393 | 95.4% |

The libraries from Table 1 were screened on a 60 member UTI panel to determine if library members had comparable or greater activity, or ability to infect, these UTI strains. The activity of the phages on each UTI strain was judged by plaque assay based on the frequency of large plaques and in liquid culture based on the ability of the phages to lyse the UTI strain and the duration of time taken for the host to recover and become insensitive to the phage as measured using optical density of the culture. If the phages with multiple substitutions had more large plaques, or if those phages prolonged the period of time taken for the liquid culture to recover, it was considered more active and capable of infecting that strain. These results are shown in Table 2. Overall, T7 bacteriophages with multiple substitutions showed enhanced activity on six of the UTI strains examined in the panel with no loss in ability to infect any UTI strains wild type can infect.

TABLE 2

PRELIMINARY ACTIVITY OF T7 BACTERIOPHAGES WITH MULTIPLE SUBSTITUTIONS

| UTI Strain ID | Preliminary Activity of T7 Bacteriophages with Multiple Substitutions |
|---|---|
| 1 | No Apparent Activity |
| 2 | No Apparent Activity |
| 3 | No Apparent Activity |
| 4 | No Apparent Activity |
| 5 | No Apparent Activity |
| 6 | No Apparent Activity |
| 7 | No Apparent Activity |
| 8 | No Apparent Activity |
| 9 | Comparable Activity to Wild Type |
| 10 | No Apparent Activity |
| 11 | No Apparent Activity |
| 12 | No Apparent Activity |
| 13 | No Apparent Activity |
| 14 | No Apparent Activity |
| 15 | No Apparent Activity |
| 16 | No Apparent Activity |
| 17 | No Apparent Activity |
| 18 | No Apparent Activity |
| 19 | Better Activity Compared to Wild Type |
| 20 | No Apparent Activity |
| 21 | Comparable Activity to Wild Type |
| 22 | No Apparent Activity |
| 23 | No Apparent Activity |
| 24 | No Apparent Activity |
| 25 | No Apparent Activity |
| 26 | Better Activity Compared to Wild Type |
| 27 | No Apparent Activity |
| 28 | No Apparent Activity |
| 29 | No Apparent Activity |
| 30 | Comparable Activity to Wild Type |
| 31 | Comparable Activity to Wild Type |
| 32 | Comparable Activity to Wild Type |
| 33 | Better Activity Compared to Wild Type |
| 34 | No Apparent Activity |
| 35 | No Apparent Activity |
| 36 | No Apparent Activity |
| 37 | No Apparent Activity |
| 38 | No Apparent Activity |
| 39 | No Apparent Activity |
| 40 | No Apparent Activity |
| 41 | No Apparent Activity |
| 42 | No Apparent Activity |
| 43 | Better Activity Compared to Wild Type |
| 44 | No Apparent Activity |
| 45 | No Apparent Activity |
| 46 | Better Activity Compared to Wild Type |
| 47 | Better Activity Compared to Wild Type |
| 48 | No Apparent Activity |
| 49 | No Apparent Activity |
| 50 | No Apparent Activity |
| 51 | No Apparent Activity |
| 52 | No Apparent Activity |
| 53 | No Apparent Activity |
| 54 | No Apparent Activity |
| 55 | No Apparent Activity |
| 56 | No Apparent Activity |
| 57 | No Apparent Activity |
| 58 | No Apparent Activity |
| 59 | No Apparent Activity |
| 60 | No Apparent Activity |

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

population of acceptor phages within a first host bacteria, the first host bacteria comprising a first helper plasmid and a recombination plasmid, wherein the first helper plasmid expresses the endogenous target phage gene, and the recombination plasmid comprises the mutated target phage gene and complimentary recombination sites and expresses a recombinase, wherein the recombining produces a mixed phage population comprising acceptor phages and recombined phages, wherein the recombined phages comprise the mutated target phage gene in their genomes;

selectively accumulating the recombined phages from the mixed phage population by replicating the mixed phage population within a second host bacteria, the second host bacteria comprising a second helper plasmid and a counterselection system, wherein the second helper plasmid expresses the endogenous target phage gene, wherein the counterselection system suppresses replication of the acceptor phages, and wherein replication of acceptor phages is suppressed and replication of recombined phages is amplified to provide a population of accumulated recombined phages; and replicating the population of accumulated recombined phage within a third host bacteria, without a helper plasmid, to provide the unbiased phage library, wherein the population of lytic phages lyses the first, second and third bacteria.

2. The method of claim 1, wherein the first, second or third bacteria are *E. coli*, and the base population of lytic phages comprises phiX174, T1, T2, T3, T4, T5, T6 or T7 phage; wherein the first, second or third bacteria are *Salmonella* sp. and the base lytic phage comprises phiChi13, S16 or E1, wherein the first, second or third bacteria are *Yersinia* sp. and the base lytic phage comprises phiYeO3-12 or YpsP-PST; or wherein the first, second or third bacteria are *Acinetobacter* sp. and the base lytic phage comprises AP205, Fri1 or PD6A3.

3. The method of claim 1, wherein the target phage gene is associated with phage efficacy, host specificity, phage

The invention claimed is:

1. A method of preparing an unbiased mutational phage library of a target phage gene, comprising preparing a population of acceptor phages having a genome comprising recombination sites by providing a base population of lytic phages having a lytic phage genome, removing an endogenous target phage gene from the lytic phage genome, and inserting the recombination sites into the lytic phage genome;

recombining a mutated target phage gene into a portion of the population of acceptor phages by replicating the stability, disruption of biofilms, delivery of genetic markers, host resistance, editing of microbial communities, timed lysis, biocontrol of foodborne pathogens, antibiotic-resistant bacteria, or a combination thereof.

4. The method of claim 1, wherein the acceptor phage recombination sites are loxP, FRT, phiC31/aat, RS or rox recombination sites.

5. The method of claim 1, wherein the acceptor phage recombination sites are loxP recombination sites.

6. The method of claim 1, wherein the first, second and third bacteria comprise, independently, *E. coli, Acineto-* bacter species, *Staphylococcus* species, *Enterococcus* species, *Salmonella* species, *Shigella* species, *Streptococcus* species, *Clostridium* species, *Lactobacillus* species, *Neisseria* species, *Proteus* species, *Pseudomonas* species, and *Haemophilus* species.

7. The method of claim 1, wherein the mutated target phage gene is a variant library member, wherein the variant library includes mutation of one or more positions in a genomic locus, a coding region or a non-coding region.

8. The method of claim 1, wherein the counterselection system comprises a counter selection plasmid comprising CRISPR-Cas9.

9. The method of claim 1, wherein the counterselection system comprises restriction modification, phage growth limitation, DISARM, or Ocr from T7 phage.

10. The method of claim 1, further comprising genomic sequencing of the unbiased phage library.

11. The method of claim 1, wherein the mutated target phage gene comprises 1 to 10 substitutions compared to the endogenous target gene.

12. The method of claim 1, wherein the mutated target phage gene comprises a domain not found in the endogenous target gene.

13. The product of the process of claim 1, wherein the unbiased phage library includes recombinase sites flanking the mutated target phage gene.

* * * * *

SEQUENCE LISTING

<160> NUMBER OF SEQ ID NOS: 1

<210> SEQ ID NO 1
<211> LENGTH: 34
<212> TYPE: DNA
<213> ORGANISM: Artificial Sequence
<220> FEATURE:
<223> OTHER INFORMATION: loxP sequence with an 8 base sequence flanked by symmetric 13 base sequences

<400> SEQUENCE: 1
ataacttcgt ataatgtatg ctatacgaag ttat                34